(12) United States Patent
Lenz et al.

(10) Patent No.: US 9,605,251 B2
(45) Date of Patent: Mar. 28, 2017

(54) COMPOSITIONS, METHODS AND USES FOR STIMULATING IMMUNE RESPONSES

(75) Inventors: Laurel L. Lenz, Denver, CO (US); Rebecca L. Schmidt, Glendale, CO (US)

(73) Assignee: NATIONAL JEWISH HEALTH, Denver, CO (US)

( * ) Notice: Subject to any disclaimer, the term of this patent is extended or adjusted under 35 U.S.C. 154(b) by 581 days.

(21) Appl. No.: 13/509,269

(22) PCT Filed: Nov. 10, 2010

(86) PCT No.: PCT/US2010/056266
§ 371 (c)(1),
(2), (4) Date: Apr. 25, 2013

(87) PCT Pub. No.: WO2011/060093
PCT Pub. Date: May 19, 2011

(65) Prior Publication Data
US 2013/0259826 A1 Oct. 3, 2013

Related U.S. Application Data

(60) Provisional application No. 61/259,890, filed on Nov. 10, 2009.

(51) Int. Cl.
| | |
|---|---|
| *C12N 9/52* | (2006.01) |
| *A61K 39/39* | (2006.01) |
| *A61K 38/20* | (2006.01) |
| *A61K 39/02* | (2006.01) |
| *A61K 45/06* | (2006.01) |
| *A61K 39/00* | (2006.01) |

(52) U.S. Cl.
CPC .............. *C12N 9/52* (2013.01); *A61K 38/208* (2013.01); *A61K 39/0208* (2013.01); *A61K 39/39* (2013.01); *A61K 45/06* (2013.01); *A61K 2039/55516* (2013.01); *A61K 2039/57* (2013.01)

(58) Field of Classification Search
None
See application file for complete search history.

(56) References Cited

U.S. PATENT DOCUMENTS

| 5,932,415 A | 8/1999 | Schubert et al. |
| 2008/0206269 A1 | 8/2008 | Mukamolova et al. |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
UniProt Q4TVQ4 (downloaded from http://www.uniprot.org/uniprot/Q4TVQ4; sequence last updated Jul. 19, 2005.).*
Pfam domain diagram showing the domain conformation; downloaded from http://pfam.xfam.org/protein/Q4TVQ4; sequence last updated Jul. 19, 2005.*
Anantharaman, et al., Evolutionary history, structural features and biochemical diversity of the NlpC/P60 superfamily of enzymes, Genome Biology, vol. 4, Issue 2, (Feb. 2003).
Humann, et al., Expression of the p60 autolysin enhances NK cell activation and is required for listeria monocytogenes expansion in IFN-gamma—responsive mice. J. Immunol. Feb. 2007, vol. 178. No. 4, pp. 2407-2414.
International Search Report and Written Opinion issued in PCT/US2010/056266, mailed Apr. 27, 2011, pp. 1-13.
Jiang, et al. Listeria monocytogenes strain 10403S lap (lap) gene, complete cds. GenBank. Accession No. DQ054587. (Aug. 2006). http://www.ncbi.nlm.nih.gov/nuccore/dq054587.
Seikguchi, et al. Effective Combination Therapy Using Interferon-γ and Interleukin-2 for Disseminated Mycobacterium avium Complex Infection in a Pediatric Patient with AIDS, Clin. Infect. Dis., Dec. 2005, vol. 41, No. 11, pp. 104-106.
Wuenscher, et al., The iap Gene of Listeria monocytogenes is Essential for Cell Viability, and Its Gene Product, p60, Has Bacteriolytic Activity. Journal of Bacteriology, Jun. 1993, pp. 3491-3501.

* cited by examiner

*Primary Examiner* — Brian J Gangle
*Assistant Examiner* — Andrea McCollum
(74) *Attorney, Agent, or Firm* — Faegre Baker Daniels LLP

(57) ABSTRACT

Embodiments herein report compositions, methods and uses for inducing an innate immune response in a subject. Embodiments herein also generally report compositions, methods and uses for bacterial-derived peptides to induce an innate immune response in a subject having a bacterial or viral disorder and/or cancer. In certain embodiments, compositions herein concern derivatives of p60 protein of *Listeria monocytogenes*.

20 Claims, 11 Drawing Sheets

FIGS. 1A-D
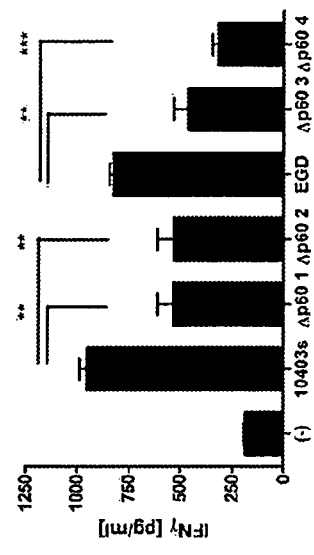
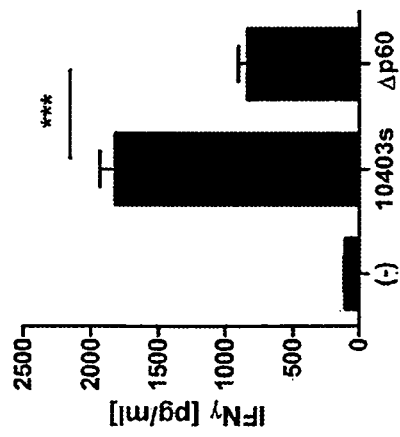
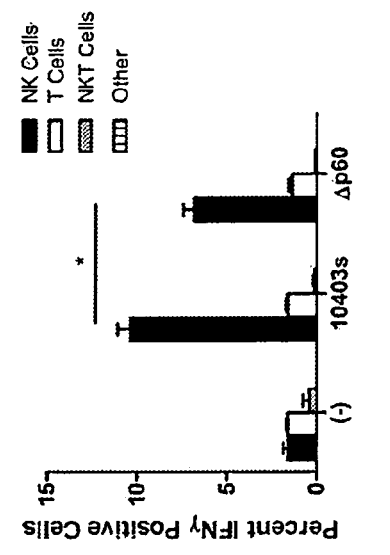
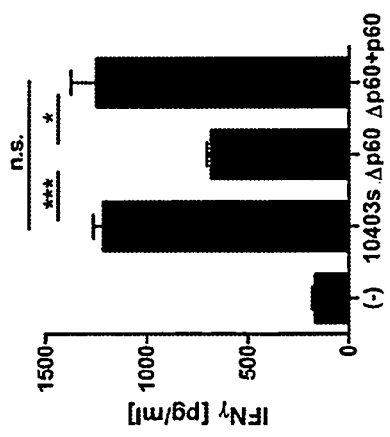

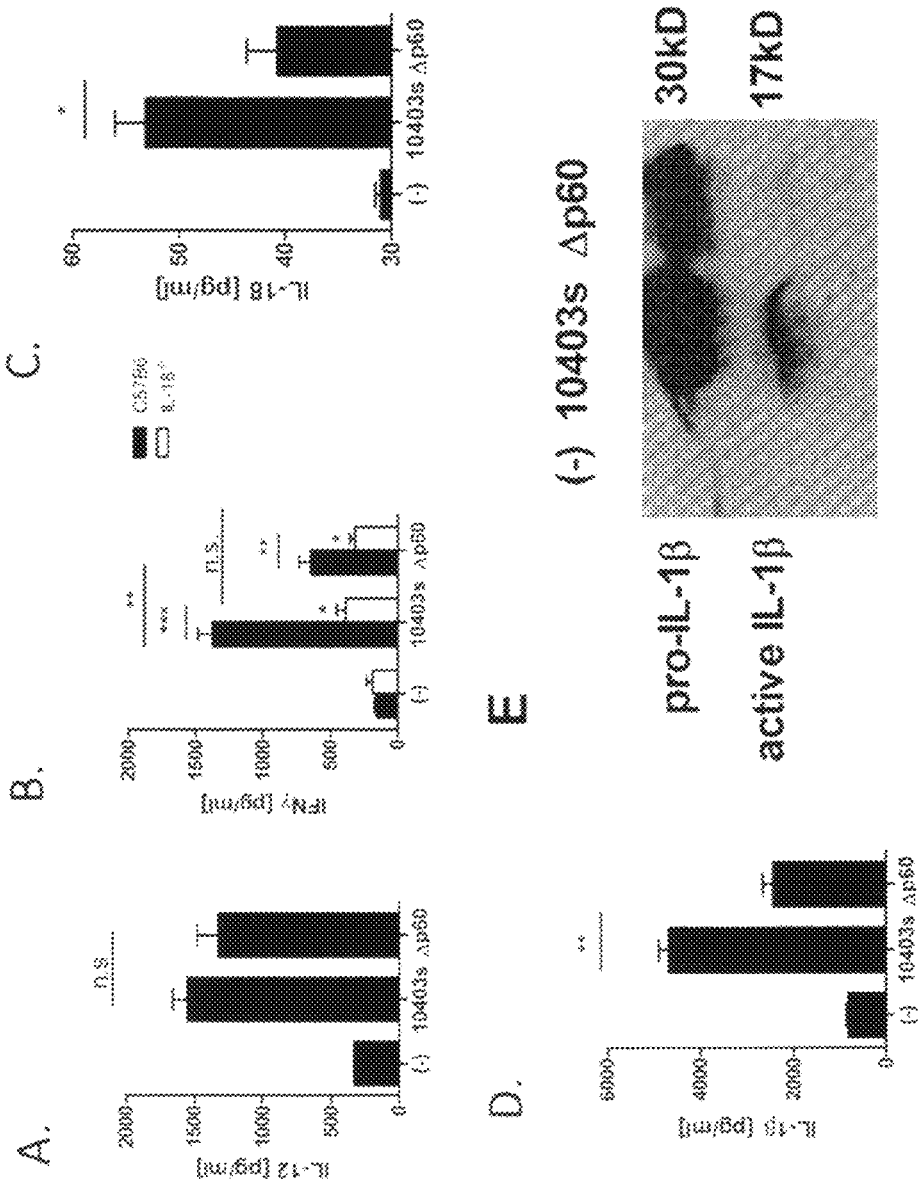
FIGS. 2A-E

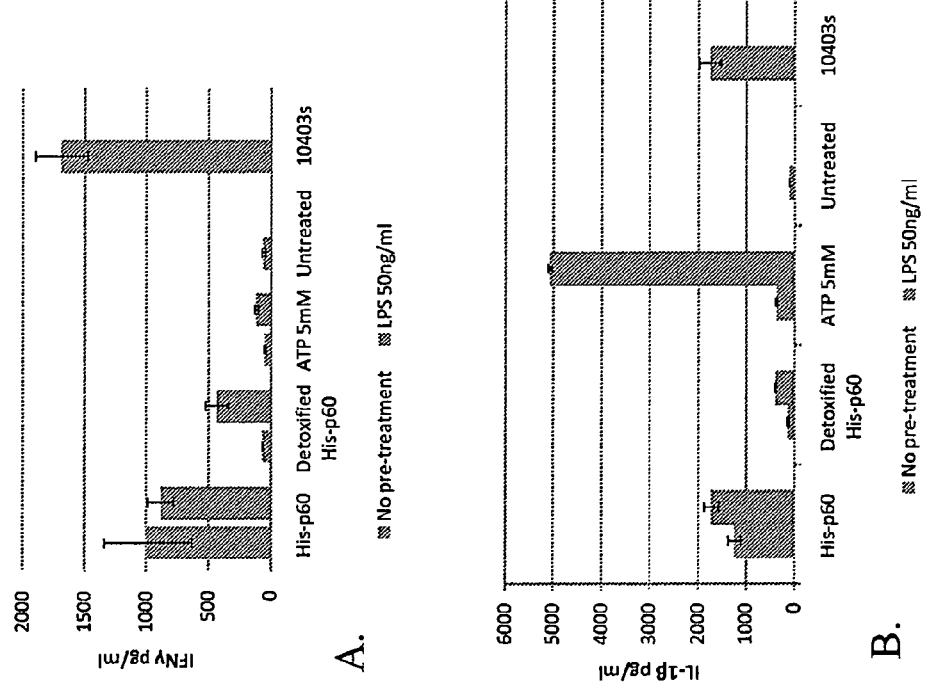
FIGS. 3A-B

FIGS. 4A-E
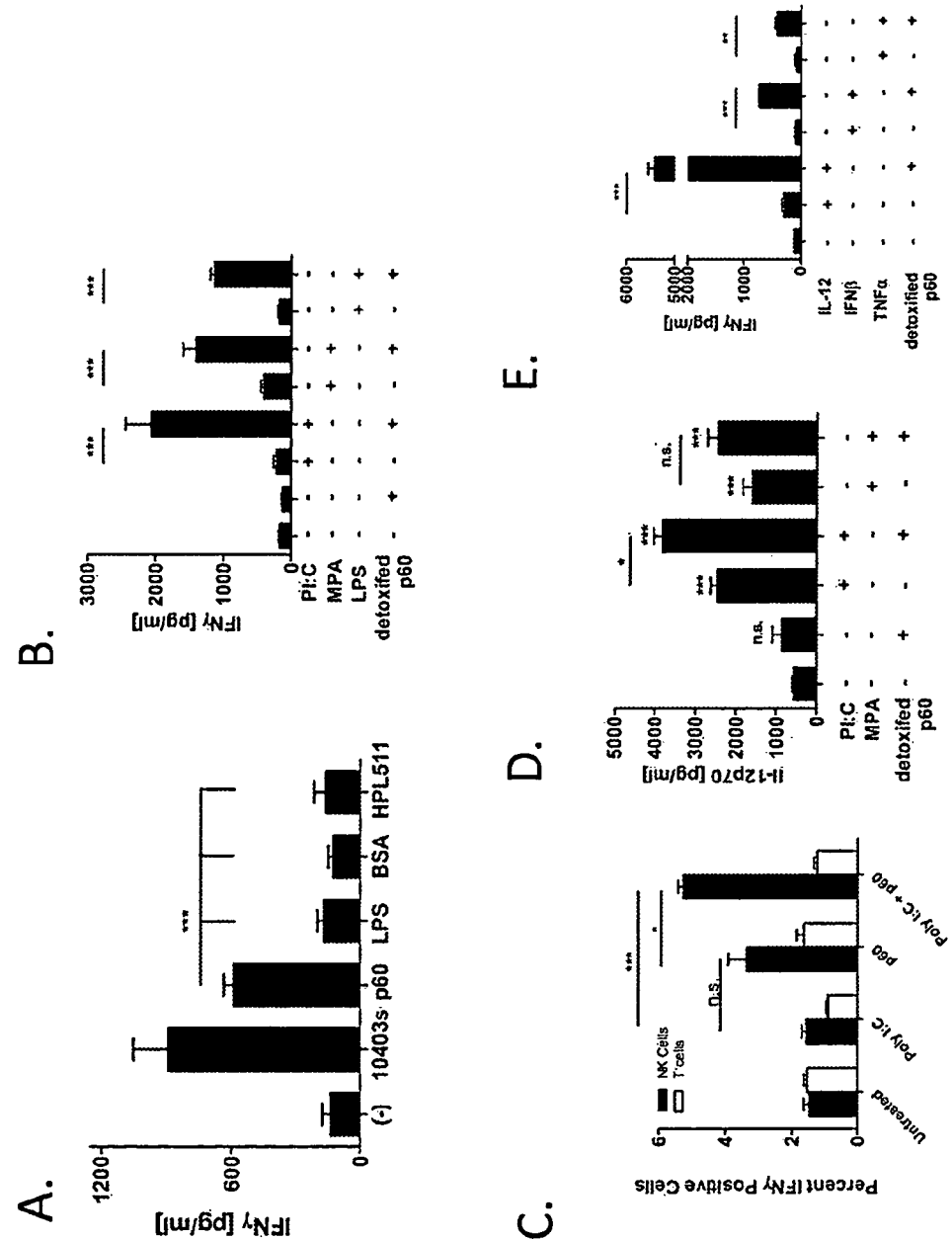

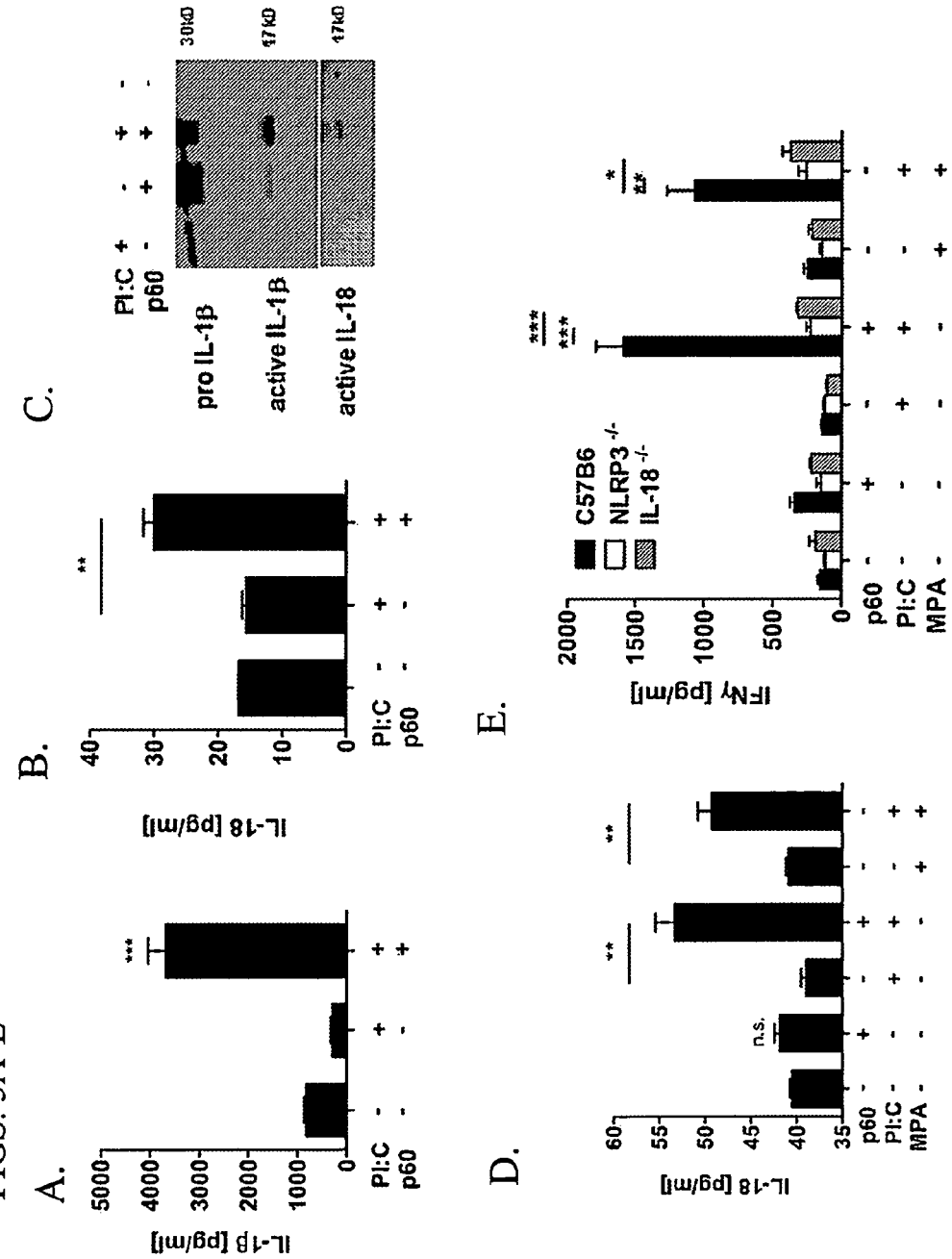
FIGS. 5A-E

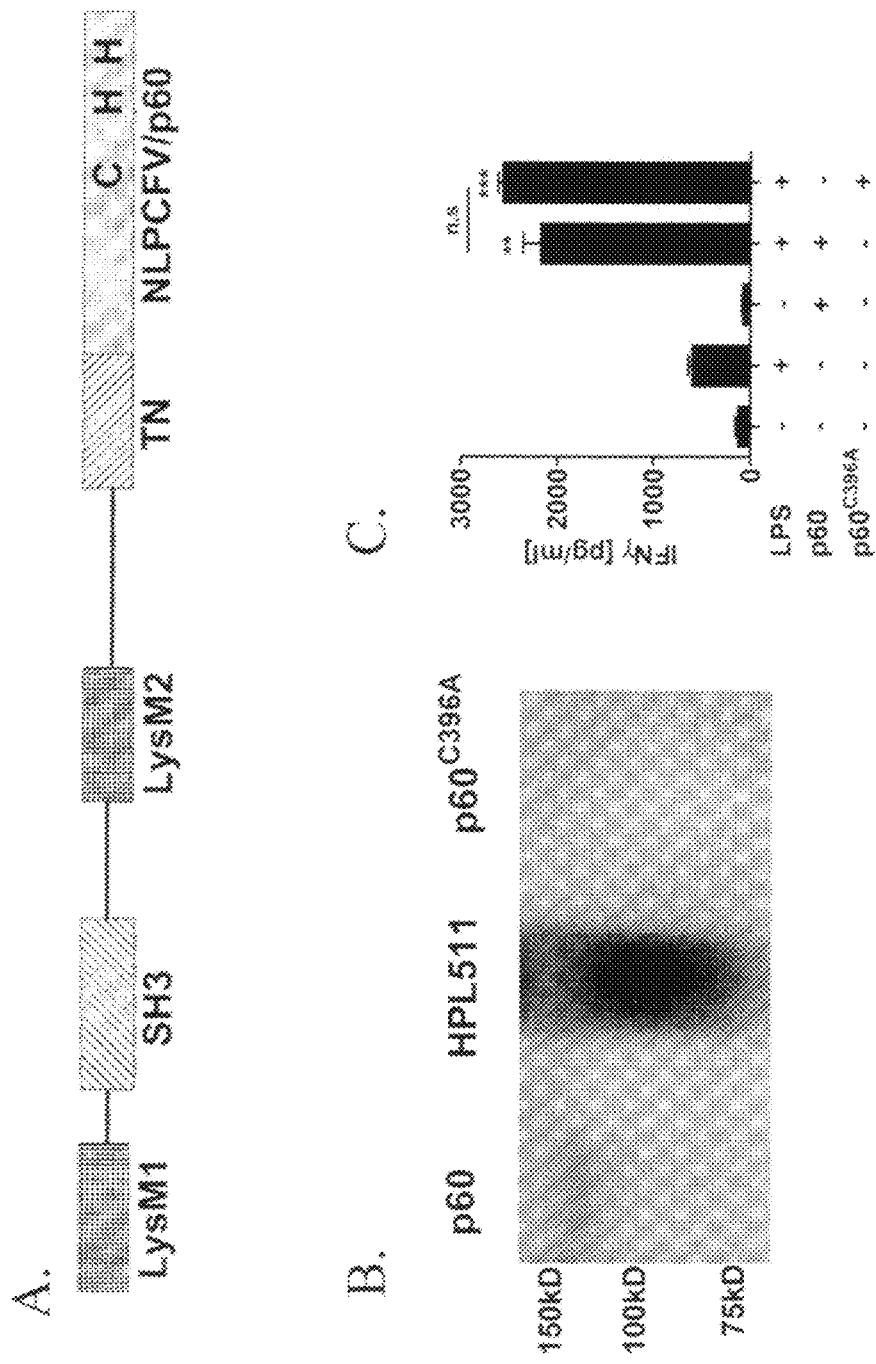
FIGS. 6A-C

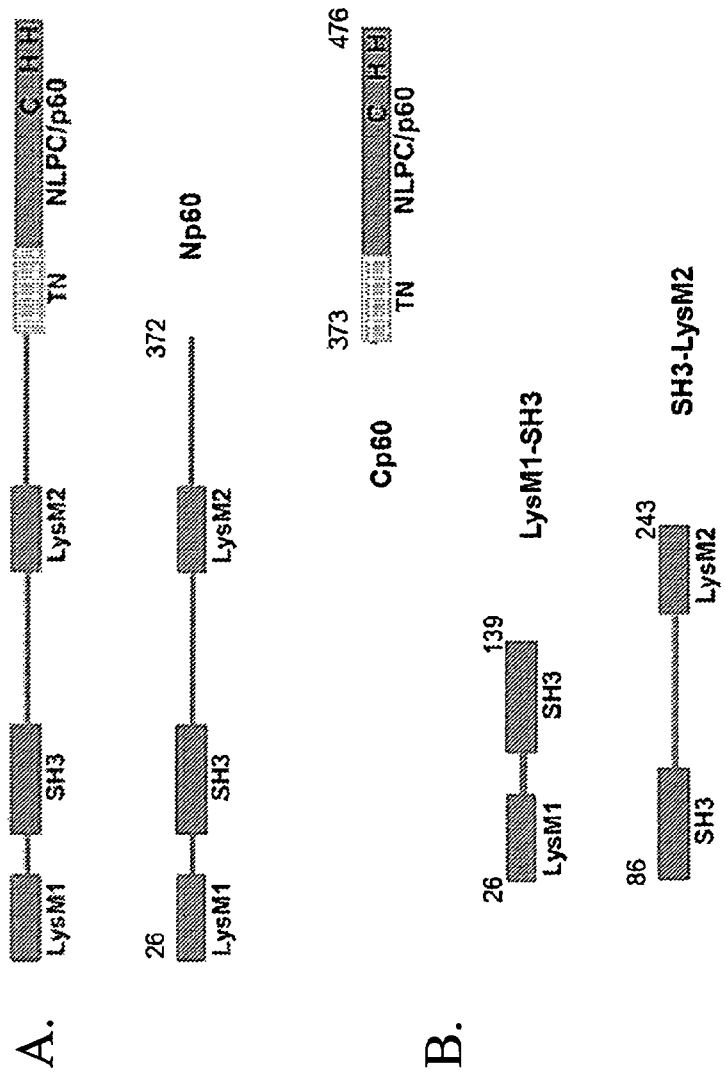
FIGS. 7A-B

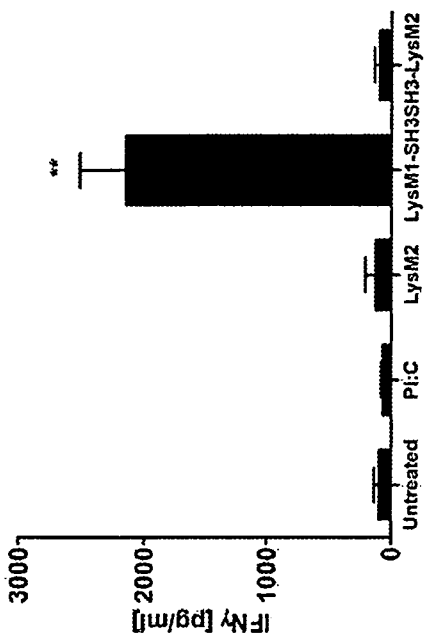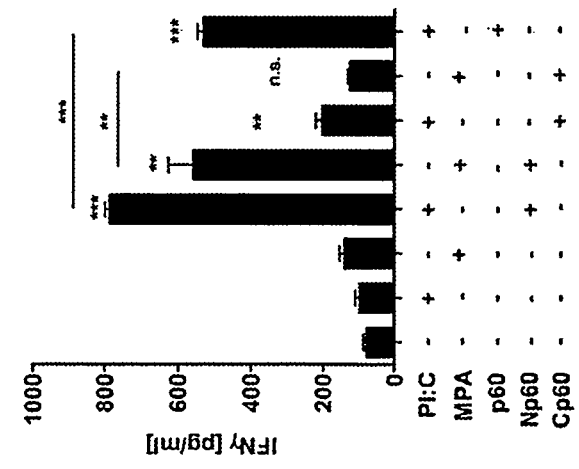
FIGS. 7C-D

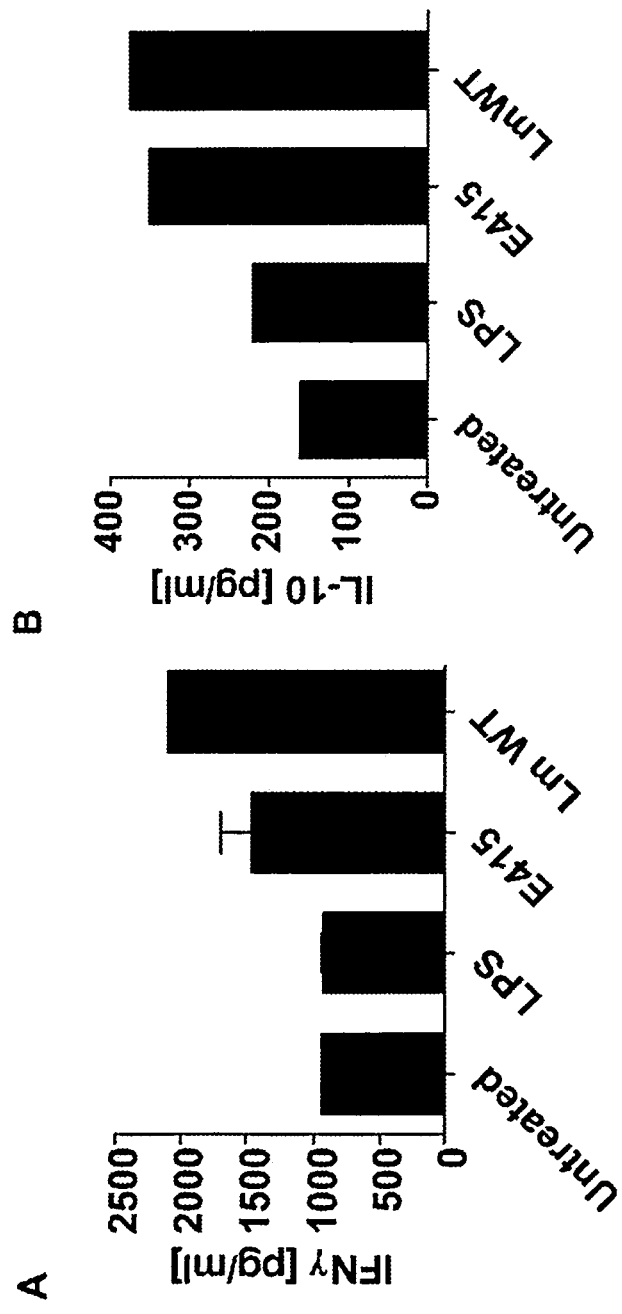
FIGS. 10A-B

COMPOSITIONS, METHODS AND USES FOR STIMULATING IMMUNE RESPONSES

RELATED APPLICATIONS

This application is a U.S. 371 application that claims priority to PCT application PCT/US2010/056266, filed Nov. 10, 2010, which claims the benefit under 35 U.S.C. §119(e) of provisional U.S. patent application Ser. No. 61/259,890, filed on Nov. 10, 2009. These applications are incorporated herein by reference in its their entirety for all purposes.

STATEMENT REGARDING FEDERALLY FUNDED RESEARCH

Embodiments disclosed herein have been supported in part by National Institutes of Health, NIAID, R01 Grant No. AI065638. The government has certain rights to embodiments of this invention.

FIELD

Embodiments herein report methods and uses for inducing an immune response in a subject in need thereof. Embodiments of the present invention also generally report compositions, methods and uses for bacterial-derived peptides to induce an immune response in a subject having a disorder. Other embodiments report compositions and methods of use to maintain a healthy pregnancy. In certain embodiments, compositions, methods and uses herein concern peptide derivatives or mutants of p60 protein of *Listeria monocytogenes*.

BACKGROUND

NK cells are large granular lymphocytes that help control infections and tumors and regulate autoimmune responses. Once activated, NK cells have both cytotoxic and cytokine-secreting effector functions. NK cells employ Fas, TRAIL, and secretion of perforin and granzyme B to induce apoptosis or lysis of distressed somatic cells. NK cells also produce cytokines and are a major source of IFNγ at early times after viral and bacterial infections. Secreted IFNγ enhances cytotoxicity against tumor cells, induces CD4 Th1 differentiation, stimulates antiviral responses, and activates macrophages to become more bactericidal to intracellular pathogens.

Stimulation of innate immune responses can be used to treat a variety of disorders. In addition, stimulation of innate immune responses can be used to improve adaptive immune responses to certain agents and/or vaccines to improve responsiveness to these agents.

SUMMARY

Embodiments herein report compositions, methods and uses for inducing an immune response in a subject in need thereof. This application also generally reports compositions, methods and uses for bacterial-derived peptides to induce an immune response in a subject having a bacterial or viral disorder (e.g. an intracellular infection), receiving a vaccination, having an autoimmune disorder and/or having cancer. Some embodiments relate to compositions, methods and uses of *Listeria monocytogenes* (Lm) protein, p60. In other embodiments, compositions herein concern peptide derivatives or mutants of p60 protein of *Listeria monocytogenes*. In accordance with some of these embodiments, Lm p60 protein derivatives or mutants can be used to stimulate immunoregulatory cytokines such as IFNγ, IL-1β, TNFα, IL-12, IL-1β, IL-15, Il-2, and IL-18 production or other cytokine production in order to boost or regulate an immune response in a subject in need thereof. Other embodiments include compositions and methods disclosed herein to stimulate dendritic cell (DC) and/or NK cell activation in a subject having a disorder or in need of an immune boost.

Some embodiments include novel compositions and peptides derived from Lm p60. In one exemplary method, a mutant derived from Lm p60 includes, but is not limited to, p60 (C389A) where cysteine in position 389 of p60 can be mutated to an alanine (referred to as "E415"); Np60 which includes an N-terminal amino acid peptide derived from p60; Cp60 which includes a C-terminal peptide derived from p60 or other peptide derived from p60 having immune stimulation capabilities. Some peptide derivations have domain regions described herein. In some embodiments, N-terminal derived peptides of use herein can include one or more domains selected from LysM and SH3 domains. Other embodiments can include compositions of endotoxin-free recombinant p60 protein or purified p60 for inducing inflammasome activation and/or secretion of mature IL-1β and IL-18 in a subject in need thereof. These compositions may further include additional agents or factors (e.g. inflammatory cytokines, BMDCs and TLR agonists) in order to activate DC and/or NK cells to a predetermined level in a subject in need thereof.

In certain embodiments, compositions and methods disclosed herein can be used in combinations with vaccinations in order to boost immune responses to a vaccine in a subject. Alternatively, compositions and methods disclosed herein may be used to manipulate an immune response in a subject having an autoimmune disorder or cancer. Compositions and methods disclosed herein can be used alone or in combination with methods and compositions known in the art to treat a subject having an autoimmune disorder or cancer. In certain embodiments, compositions and methods disclosed herein can be used to target cells infected by a microorganism or a tumor cell in order to destroy the cell(s) (e.g. by lysing the cell) in a subject having an infection or a tumor.

Other embodiments report compositions and methods of use to maintain a healthy pregnancy.

Yet other embodiments report compositions that can be used in a kit for treating conditions disclosed herein. A kit can include at least one container and at least one p60 derived peptide or mutant in a composition of use to treat conditions described.

DESCRIPTION OF ILLUSTRATIVE EMBODIMENTS

Brief Description of the Figures

The following drawings form part of the present specification and are included to further demonstrate certain embodiments of the present invention. The embodiments may be better understood by reference to one or more of these drawings in combination with the detailed description of specific embodiments presented herein.

FIGS. 1A-1D represent exemplary experiments related to p60 and its affect on NK cell activation and production of inflammatory cytokines FIGS. 2A-2E represent exemplary experiments related to p60 and its affect on inflammatory cytokine secretion.

FIGS. 3A and 3B represent exemplary experiments of effects of LPS priming on IFNγ-inducing activity to detoxified p60 and ATP stimulation.

FIGS. 4A-4E represent exemplary experiments of effects of p60 in the presence or absence of various cytokines and TLR stimulants on inflammatory cytokine production and NK cell activation.

FIGS. 5A-5E represent exemplary experiments of effects of p60 in the presence or of TLR stimulants on activation of NRLP3-dependent inflammasomes.

FIGS. 6A-6C represent p60 peptide derivatives and mutants and effect of a p60 mutant on inflammatory cytokine production.

FIGS. 7A-7D represent various peptide derivatives and mutants of p60 (A and B); and effects of some p60 peptides and mutants on inflammatory cytokine production.

FIGS. 10A and 10B represent exemplary experiments regarding in vivo administration of a mutant of p60 or wildtype *Listeria monocytogenes* (LM) and effects on cytokine production (IFNγ for FIG. 10A; IL-10 for FIG. 10B).

DETAILED DESCRIPTION

Figure 8:
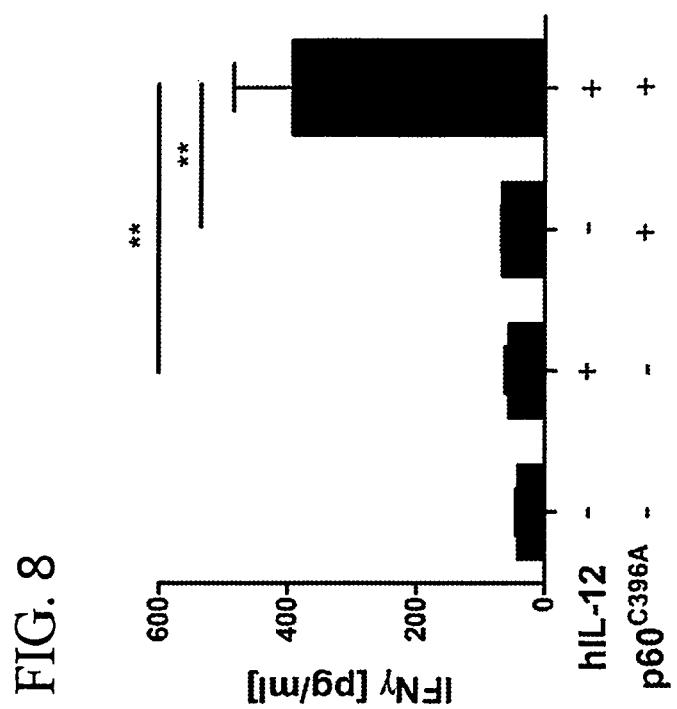
FIG. 8 represents an exemplary experiment regarding mixed cultures of human cells and effects of p60 and/or cytokines on production of an inflammatory cytokine in the mixed cultures.

In the following sections, various exemplary compositions and methods are described in order to detail various embodiments of the invention. It will be obvious to one skilled in the art that practicing the various embodiments does not require the employment of all or even some of the details outlined herein, but rather that concentrations, times, temperature and other details may be modified through routine experimentation. In some cases, well known methods or components have not been included in the description.

In accordance with embodiments of the present invention, compositions and methods disclosed herein may be used to treat a subject having a disorder. In certain embodiments, a disorder can include a bacterial or viral infection. In other embodiments, compositions and methods disclosed herein may be used to treat a subject having a vaccination in order to, for example, boost response to the vaccine by modulating immunity. In yet other embodiments, compositions and methods disclosed herein may be used to treat a subject having cancer or having an autoimmune disorder. Some embodiments concern compositions and methods for treating a pregnant female having or suspected of developing pre-eclampsia or other NK cell related disorder.

Natural Killer Cells

Natural killer cells (or NK cells) are a major component of the innate immune system. These cells are a type of cytotoxic lymphocyte. In certain roles, NK cells can play a major role in rejection of tumors and cells infected by viruses. One method that NK cells kill is by releasing small cytoplasmic granules of proteins called perforin and granzyme that can cause a target cell to go into apoptosis and die. NK cells can be defined as large granular lymphocytes (LGL). NK cells do not express T-cell antigen receptors (TCR) or Pan T marker CD3 or surface immunoglobulins (Ig) B cell receptor but they usually express the surface markers CD16 (FcγRIII) and CD56 in humans. About 80% of NK cells also express CD8. Natural Killer cell activity is tightly regulated. NK cells must receive an activating signal, which can come in a variety of forms. Some activators of NK cells can include, but are not limited to cytokines, Fc Receptor and Activating and inhibitory receptors. Cytokines can play an important role in NK cell activation. Cytokines are typically stress-molecules, released by cells for example, upon viral infection. They can serve to signal the NK cell when viral pathogens are present. NK cells express the FcR molecule, an activating biochemical receptor that binds the Fc portion of antibodies. This allows NK cells to target cells against which a humoral response has been mobilized and to lyse cells through Antibody-dependent cellular cytotoxicity (ADCC). NK cells also express a variety of receptors that serve to either activate or suppress their cytolytic activity. These receptors bind to various ligands on target cells, both endogenous and exogenous, and have an important role in regulating the NK cell response.

NK cells are attractive targets for therapy in cancer and other diseases. Activated NK cells can directly kill tumor or virus infected cells as well as secrete cytokines such as IFNγ that can stimulate effective anti-tumor and anti-viral innate immune responses. NK cells may also play a regulatory role in Type I diabetes and multiple sclerosis. It is contemplated herein that any one of these conditions may be treated or modulated using compositions and methods disclosed herein. In addition, NK cells may modulate other disease conditions associated with inflammation and pre-eclampsia. NK cells regulate immune and autoimmune T cell responses through production of IFNγ or inhibitory cytokines such as IL-10 and can suppress autoreactive B cells. NK cells can also kill T cells that do not show sufficient self signal, and anti CD94 antibodies have been effective at stimulating NK cells to kill CD4+ cells. Therefore, therapies that elicit NK cell activation may be useful to treat a variety of diseases and immune disorders. For most NK cell therapies, NK cells are adoptively transferred into animals or patients—for example to elicit antitumor responses. While this approach has been effective in some cases, the process of expanding and activating NK cells in vitro is laborious and expensive. In this regard, the use of p60 to specifically activate NK cells may have therapeutic utility. Cytokines such as IL-2, IL-12 IL-18, and type 1 IFNs have been used to stimulate NK cells in anti-tumor models. Thus, these agents may be used at reduced levels (e.g. non-toxic levels) in combination with compositions disclosed herein to treat a subject having cancer (e.g. haematologic and metastatic cancers).

Cancers contemplated herein include, but are not limited to, bladder cancer, leukemia, lymphoma, Hodgkin's disease, Waldenstrom's disease, multiple myeloma, melanoma, oral, cancers of the prostate, breast, lung, colon, head and neck, esophagus, stomach, pancreas, liver, kidney, testis, ovary, endometrial lining, uterus, cervix, thyroid, brain.

In certain embodiments, a mouse model can be used to test compositions and methods described herein. In certain examples, mouse models exist for testing E415, Np60, and LysM1-SH2 derived from p60. These models include, but are not limited to, orthotopic tumorigenesis assays of bladder, bone, brain, breast, esophageal, colon, gastric, liver, lung, lymphomas, oral, ovarian, pancreatic, renal, subcutaneous, and uterine cancer cells. Injection of the aforementioned cancer cells into blood vessels can permit study of metastatic cancers. Mice with transgenic mutations, and/or universal or conditional knock outs of tumor suppressors and/or oncogenes can be used to study the ability of p60 and its derivatives to augment the NK immune response against endogenous, spontaneously developed cancers in vivo. Such genetic mouse models include, but are not limited to, mutations in the following genes: Kras, BCR ABL1, Ncam, Bax, Bcl2l, Fas, Fasl, MAP2k, Mdm2, Pten, Rac2, FAR1 ER1, Src, TERT, Traf1, Trp53, vHa-RAS, EGRF, IFNγ, IL-10, IL2a, IL-2b, IL-15, IL2r, IL4, IL5, Il6, IL7, Il8, Kit, Shh, Stat6, Tnf Myc, Notch, E2f2, Ing1, Ski, TLX1, Wnt1, TAg, and Rag1.

In certain aspects, it is contemplated herein that compositions (e.g. p60 derived peptides or mutants) described herein may be used exogenously to stimulate NK cells from a subject in need thereof, for example, in the presence of DC cells, for expansion. Once the NK cells are expanded, these populations may be introduced to a subject having cancer or other condition.

In some embodiments, viral or bacterial infections of cells of a subject can include, but are not limited to, HIV, EBV, feline leukemia virus, influenza, herpes viruses, hepatitis viruses, pox viruses, Polyoma viruses, Papova viruses, Circo viruses, Mimi viruses, Calici viruses, Astro viruses, Corona viruses, Paramyxo viruses, Filo viruses, Bunya viruses, Borna viruses, Papillomavirus, Adenoviruses, Parvoviruses, Reoviruses, Picornaviruses, Togaviruses, Orthomyxoviruses, Rhabdoviruses, Hepadnaviruses, Myxovirus, Pneumonia, Arenaviruses, *Salmonella, Shigella, Coxiella, Chlamydia, Rickettsia, Francisella, Yersinia, Listeria, Legionella, Rhodo coccus, Mycobacteria, Borrelia, Treponema, Ehrlichia, Afipia, Nocardia, Streptococcus, Burkholderia, Staphylococcus* or other viral or bacterial-associated infections. Other embodiments may concern a parasitic infection in a subject including, but not limited to, *plasmodium*, malaria, *Giardia, Babesia, Toxoplasma, Leishmania, Trypanosoma*, or other parasitic infection known in the art. In certain embodiments, one or more compositions disclosed herein can be used in a subject having a viral or bacterial infection. In certain embodiments, compositions (e.g. p60 derived peptide or p60 mutant compositions) described herein can be administered to a subject in order to attack and destroy viral or bacterial infected cells of the subject.

*Listeria monocytogenes*

Lm is a Gram-positive, facultative intracellular pathogen. During infection, it escapes phagosomal compartments in macrophages, dendritic cells, and other somatic cell types to replicate in the cytosol. IFNγ typically plays a protective role in immunity to Lm and other pathogens, in part by inducing macrophages to become bactericidal.

Lm p60

Lm p60 is a highly secreted Lm protein with putative endopeptidase enzymatic activity. In certain embodiments reported herein, p60-expression by Lm strains and addition of recombinant p60 protein enables IL-12 secreting dendritic cells (DCs) to promote activation of naïve NK cells. In addition, Lm p60 can activate NK cells indirectly, by binding DCs and triggering NLRP3-dependent processing and secretion of mature IL-18.

The full-length p60 protein contains an NLPC/p60 endopeptidase domain. Bacterial proteins that contain NLPC/p60 domains are thought to digest peptidoglycan (PGN), and purified p60 protein cleaves PGN weakly (see for example FIG. 8). In certain embodiments disclosed herein, purified p60 can promote inflammasome activation in DCs independent of PGN. In other embodiments, compositions of p60 of use herein can include p60 where enzymatic activity is reduced or removed, or the enzymatic region of the p60 molecule is mutated. In accordance with these embodiments, these compositions can be used to induce IL-1 or IL-18 secretion or NK cell activation.

Certain embodiments concern delivery of a pharmaceutically acceptable p60 or a p60 derived peptide or a p60 mutant (e.g. having reduced or no enzymatic activity) to a subject in need thereof. Any method known in the art for delivery of a peptide or protein agent or composition is contemplated herein. Some embodiments concern using microparticles, microspheres, nanoparticles, gelatinous delivery materials, antibodies, antibody fragments, fusion proteins, directed transfer compositions and methods and the like for delivery of any agent or any composition described herein to the subject. Certain aspects include fusing a p60 derived peptide to a targeting sequence to direct the p60-derived peptide in a subject (e.g. a subject having cancer or an infection). Other modes for administering agents or compositions disclosed herein to a subject in need thereof can include, but are not limited to, intravenous, timed-release formulations, intratraceal, by inhalation, orally, systemically or any methods known in the art. It is contemplated that the p60-derived peptide can be an N-terminal peptide having one or more domains (e.g. LysM or SH3 domain) described herein. In some embodiments, an N-terminal p60-derived peptide can include a peptide of a variety of lengths having one or more LysM and/or SH3 domain. In accordance with these embodiments, an N-terminally derived p60 peptide can have a LysM domain followed by an SH3 domain, optionally followed by an additional LysM domain. One example of an N-terminally derived p60 peptide of use in compositions and methods disclosed herein can include a LysM1 domain in combination with an SH3 domain, where the SH3 is about 5 to about 10, or about 5 to about 15 or about 10 to about 20 amino acids or more downstream from the LysM1 domain. In certain embodiments, compositions and methods herein can be used alone or in combination with other agents to activate NLRP3 inflammasomes in a subject in order to stimulate DC cells and/or NK cells in the subject. It is contemplated that it may be useful to use agents or compositions disclosed herein for ex vivo stimulation of DC cells or NK cells for introduction to a subject in need thereof.

LysM Domain

In some embodiments, a LysM (lysin motif) domain can be about 40 residues long (e.g. about 35 to about 50 amino acids). It is found in a variety of enzymes involved in bacterial cell wall degradation. The LysM domain is a widespread protein module. It was originally identified in enzymes that degrade bacterial cell walls but is also present in many other bacterial proteins. LysM domains are also found in some eukaryotic proteins, apparently as a result of horizontal gene transfer from bacteria. The available evidence suggests that the LysM domain is a general peptidoglycan-binding module. The LysM domain has a betaalphaalphabeta secondary structure with the two helices packing onto the same side of an anti-parallel beta sheet. The structure shows no similarity to other bacterial cell surface domains. A potential binding site in a shallow groove on surface of the protein has been identified SH3 Domain In eukaryotes and viruses, SH3 (Src homology 3) domains are typically protein interaction domains that frequently are involved in cell signaling. SH3 domains can be found in kinases, phospholipases, GTPases, and other enzymes. The domain is about 60 amino acids arranged into a beta-barrel secondary structure consisting of 5-6 beta strands arranged as two anti-parallel beta-sheets. This domain is conserved in prokaryotes. Bacterial SH3 homologues are found in autolysins, amidases, and kinases, and other proteins.

Some embodiments concern one or more amino acid or nucleic acid sequences of truncated peptide or nucleic acid derivatives of p60 protein (e.g. SEQ. ID NO:1 and 3) having no significant peptidoglycan digestion activity. Other embodiments concern a mutant form of p60 having no significant peptidoglycan digestion activity. In accordance with these embodiments, a composition can contain a mutant of p60 protein and the mutant can contain a mutation at any amino acid capable of reducing or eliminating peptidoglycan digestion activity, for example amino acid residue 389 of p60 where the catalyticcysteine can be mutated to an alanine or other amino acid. In yet other embodiments, p60 protein (SEQ ID NO: 2) is digested or cleaved where one half, the carboxy-terminus, or the second half, the amino-terminus, can be used in compositions and methods contemplated herein. Other embodiments concern a peptide derived from an engineered or expressed multi-domain *L. monocytogenes* p60 protein termed E415, (SEQ. ID NO:1) and compositions thereof. In certain embodiments, an amino terminus peptide of 200 amino acids or less, or 180 amino acids or less, or 160 amino acids or less, or 140 amino acids or less may be used as a treatment agent or in a composition for treatment of conditions in a subject disclosed herein.

It is contemplated herein that different *Listeria* strains can have a target catalytic region in slightly different area of their sequences. In certain embodiments, some strains have the catalytic region as disclosed in SEQ. ID NO:1. Other embodiments can include strains that have the catalytic region further downstream based on the size of p60 and other factors (e.g. secondary and tertiary considerations) in the strain (e.g. AA 396). These variations are contemplated herein and any Lm p60 protein having a mutated catalytic region or other region described herein is contemplated. Some of the derivatives and mutants described herein concern a mature processed form of p60 protein where the signal sequence has been cleaved. Other embodiments report mature and unprocessed forms of p60 for generating derivatives, mutants or making other forms of p60 (e.g. recombinant forms of p60 derivatives and mutants).

Other embodiments concern peptides derived from p60 protein. In certain embodiments, a peptide derived from p60 includes an N-terminal sequence that includes one or more LysM domains as depicted in SEQ ID NOs. 10 and 11. Some embodiments include a p60 peptide derivative from the N-terminus that includes one or more LysM domains and an SH3 domain, wherein the SH3 domain is downstream from a LysM domain. Peptide derivatives of p60 include an N-terminally derived peptide of about 200 amino acids or less, 150 amino acids or less, 100 amino acids or less etc. In other embodiments, an N-terminally derived peptide can include the entire N-terminus from amino acid 1 to amino acid 310 of p60. Alternatively, an N-terminally derived p60 peptide can include amino acid 1 to amino acid 243 with 2 LysM domains, LysM1 upstream from an SH3 and LysM2 downstream from the SH3 domain. In other embodiments, a peptide derivative of p60 can include a motif as depicted in SEQ ID NO: 12 represented as Xaa $_{(1-10)}$GDT Xaa $_{(1-5)}$ WXaa$_{(1-5)}$KXaa$_{(5-15)}$NNLXaa$_{(1-10)}$ VXaaGQKL Xaa$_{(1-5)}$, (SEQ ID NO:28).

In some embodiments, compositions and methods disclosed herein may be used to treat a disorder in a subject by, for example, inducing an innate immune response in the subject. Other embodiments can include administering compositions disclosed herein to a subject to induce or activate NK cells in the subject or inducing a subject's harvested NK cell to activate ex vivo and then introducing the activated NK cells to the subject. In certain embodiments, compositions herein may include a composition capable of priming naïve NK cells in a subject simultaneously or prior to administering a p60 derivative composition to the subject. In accordance with these embodiments, a priming composition may include an LPS-like solution, a TLR agonist solution, for example. polyinosinic:polycytidylic acid (PI:C), monophosphoryl lipid A or other known LPS-like compositions. Some embodiments include compositions and combination compositions for inducing IFNγ production in a subject. Other embodiments can include compositions described herein for inducing IL-1β and/or IL-18 production and/or secretion by for example, priming caspase-1 inflammasomes, to induce secretion of these cytokines or other cytokines capable of inducing an immune responses in a subject.

Yet other embodiments can include administering one or more TLR agonist compositions to a subject in need thereof prior to or simultaneously with administering compositions disclosed herein to the subject. In accordance with these embodiments, a subject may have a viral or bacterial disorder, an autoimmune condition or cancer or other condition described herein. Compositions contemplated of use for the subject in combination with TLR agonist compositions can include a p60 mutant or p60-derived peptide. Various TLR agonists may be used for priming NK cells that may further allow IFNγ release. TLR agonist contemplated of use herein can include, but are not limited to, poly I:C (PI:C), LPS, non-toxic LPS analog monophosphoryl LipidA (MPA), Pam3CSK4, Flagellin, MALP-2, Imiquimod, Imidazoquinoline, Resiquimod, CpG DNA, ssRNA, Zymosan, poly A:T, gardiquimond, hylauronic acid fragments, Kdo-2 Lipid A, Loxoribine and other TLR agonists known in the art.

Some embodiments concern using p60, p60-derived peptides or nucleic acids and/or p60 mutants in combination with one or more immunoregulatory cytokine(s). Immunoregulatory cytokines contemplated of use herein include, but are not limited to, IL-12, IL-18, TNFα, IFNα/β IL-1α, IL-1β, IL-6, LIF, OSM, CTNF, TGF-β, GM-CSF, IL-10, IL-11, IL-12, IL-15, IL-23, IL-8, IL-2, MAF, MMIF, MCF, LMIF, HRF, G-CSF, M-CSF and other immunoregulatory cytokines known in the art. Other combinations of use for in vivo or ex vivo stimulation of NK cells in a subject in need thereof can include antibodies to NK cells, for example, antibodies to NK cell surface proteins may be used to activate NK cells.

Compositions disclosed herein may be used alone in one or more doses, for example, once monthly, once weekly, bi-weekly, once daily, two times daily etc. In certain embodiments, a single dose may be administered of compositions disclosed herein in order to avoid antibody reactions or other potentially adverse reactions. In addition, compositions may be used in combination with other therapies known in the art such as vaccinations, cancer therapies, anti-viral therapies, anti-autoimmune therapies, anti-bacterial therapies or anti-pre-eclampsia therapies.

In certain embodiments, about 10-30 µg/ml or about 10-100 µg/ml of a peptide or mutant peptide contemplated herein can be used to activate NK cell ex vivo. In other embodiments, it is contemplated that about 10-500 µg per mice, about 10-500 mg per animals for small mammals and primates, and about 100 to about 1500 mg per human of average size can be administered to the subject having a condition by any method disclosed herein in order to activate the subject's immune system for treating the condition.

Proteins and peptides disclosed herein can be purified fully or partially by any method known in the art. Peptide fragments derived from p60 protein can be generated by cleaving the native molecule or synthesizing peptides or other methods known in the art for generating peptides of use herein. In addition, fusion peptides can be generated by any method known in the art (e.g. fusing a peptide disclosed herein to a targeting agent capable of directing treatment in a subject to a tumor for destruction.)

It is contemplated herein that peptides and mutants described herein in addition to their nucleic acid counterparts may be generated by any methods known in the art. In certain embodiments, peptides described herein may be cloned, expressed and wholly or partially purified for use in certain compositions and methods presented.

DNA sequence encoding the mature p60 protein from *L. monocytogenes* strain 10403s

```
                                            (SEQ ID NO: 4)
ACT GTA GTA GTC GAA GCT GGT GAT ACT CTT TGG GGT

ATC GCA CAA AGT AAA GGG ACT ACT GTT GAC GCA ATT

AAA AAA GCA AAC AAT TTA ACA ACA GAT AAA ATC GTA

CCA GGT CAA AAA TTA CAA GTA AAT AAT GAG GTT GCT

GCT GCT GAA AAA ACA GAG AAA TCT GTT AGC GCA ACT

TGG TTA AAC GTC CGT ACT GGC GCT GGT GTT GAT AAC

AGT ATT ATT ACG TCC ATC AAA GGT GGA ACA AAA GTA

ACT GTT GAA ACA ACC GAA TCT AAC GGC TGG CAC AAA

ATT ACT TAC AAC GAT GGA AAA ACT GGT TTC GTT AAC

GGT AAA TAC TTA ACT GAC AAA GCA GTA AGC ACT CCA

GTT GCA CCA ACA CAA GAA GTG AAA AAA GAA ACT ACT

ACT CAA CAA GCT GCA CCT GTT GCA GAA ACA AAA ACT

GAA GTA AAA CAA ACT ACA CAA GCA ACT ACA CCT GCG

CCT AAA GTA GCA GAA ACG AAA GAA ACT CCA GTA ATA

GAT CAA AAT GCT ACT ACA CAC GCT GTC AAA AGC GGT

GAC ACT ATT TGG GCT TTA TCC GTA AAA TAC GGT GTT

TCT GTT CAA GAC ATT ATG TCA TGG AAT AAT TTA TCT

TCT TCT TCT ATT TAT GTA GGT CAA AAG CTT GCT ATT

AAA CAA ACT GCT AAC ACA GCT ACT CCA AAA GCA GAA

GTG AAA ACG GAA GCT CCA GCA GCT GAA AAA CAA GCA

GCT CCA GTA GTT AAA GAA AAT ACT AAC ACA AAT ACT

GCT ACT ACA GAG AAA AAA GAA ACA GCA ACG CAA CAA

CAA ACA GCA CCT AAA GCA CCA ACA GAA GCT GCA AAA

CCA GCT CCT GCA CCA TCT ACA AAC ACA AAT GCT AAT

AAA ACG AAT ACA AAT ACA AAT ACA AAC AAT ACT AAT

ACA CCA TCT AAA AAT ACT AAT ACA AAC TCA AAT ACT

AAT ACG AAT ACA AAC TCA AAT ACG AAT GCT AAT CAA

GGT TCT TCC AAC AAT AAC AGC AAT TCA AGT GCA AGT

GCT ATT ATT GCT GAA GCT CAA AAA CAC CTT GGA AAA

GCT TAT TCA TGG GGT GGT AAC GGA CCA ACT ACA TTT

GAT TGC TCT GGT TAC ACT AAA TAT GTA TTT GCT AAA

GCG GGT ATC TCC CTT CCA CGT ACA TCT GGC GCA CAA

TAT GCT AGC ACT ACA AGA ATT TCT GAA TCT CAA GCA

AAA CCT GGT GAT TTA GTA TTC TTC GAC TAT GGT AGC

GGA ATT TCT CAC GTT GGT ATT TAT GTT GGT AAT GGT

CAA ATG ATT AAC GCG CAA GAC AAT GGC GTT AAA TAC

GAT AAC ATC CAC GGC TCT GGC TGG GGT AAA TAT CTA

GTT GGC TTC GGT CGC GTA TAA
```

Amino acid sequence of the mature p60 protein from *L. monocytogenes* strain 10403s

```
                                            (SEQ ID NO: 2)
T V V V E A G D T L W G I A Q S K G T T V D A I K

K A N N L T T D K I V P G Q K L Q V N N E V A A A

E K T E K S V S A T W L N V R T G A G V D N S I I

T S I K G G T K V T V E T T E S N G W H K I T Y N

D G K T G F V N G K Y L T D K A V S T P V A P T Q

E V K K E T T T Q Q A A P V A E T K T E V K Q T T

Q A T T P A P K V A E T K E T P V I D Q N A T T H

A V K S G D T I W A L S V K Y G V S V Q D I M S W

N N L S S S S I Y V G Q K L A I K Q T A N T A T P

K A E V K T E A P A A E K Q A A P V V K E N T N T

N T A T T E K K E T A T Q Q Q T A P K A P T E A A

K P A P A P S T N T N A N K T N T N T N T N N T N

T P S K N T N T N S N T N T N T N S N T N A N Q G

S S N N N S N S S A S A I I A E A Q K H L G K A Y

S W G G N G P T T F D C S G Y T K Y V F A K A G I

S L P R T S G A Q Y A S T T R I S E S Q A K P G D

L V F F D Y G S G I S H I G I Y V G N G Q M I N A Q

D N G V K Y D N I H G S G W G K Y L V G F G R V
```

The following mutant sequences and peptides derived from p60 protein are contemplated for compositions and methods described herein. It is contemplated that one or more of these mutants or peptides can be used alone or in combination to activate DC or NK cells and/or induce inflammatory cytokines. In certain embodiments, a peptide derivative of p60 can include one or more peptide of 80% or more homology to E415 (SEQ ID NO: 1); or 80% or more homology to SEQ ID No. 14, an N-terminal derived peptide of p60 terminating prior to the TN repeat or one or more peptide of 80% or more homology to SEQ. ID. NO: 8.

It is contemplated herein that peptides and mutants disclosed herein also include peptides and mutants that are at least 80% homologous or at least 85% homologous, or at least 90% homologous or at least 95% homologous or about 99% homologous to peptides and mutants described in some embodiments of the present invention. Some of these peptides and mutants are depicted below.

DNA sequence for the E415 protein (mature p60 gene from 10403S with codon change in bold)

(SEQ ID NO: 3)
ACT GTA GTA GTC GAA GCT GGT GAT ACT CTT TGG GGT

ATC GCA CAA AGT AAA GGG ACT ACT GTT GAC GCA ATT

AAA AAA GCA AAC AAT TTA ACA ACA GAT AAA ATC GTA

CCA GGT CAA AAA TTA CAA GTA AAT AAT GAG GTT GCT

GCT GCT GAA AAA ACA GAG AAA TCT GTT AGC GCA ACT

TGG TTA AAC GTC CGT ACT GGC GCT GGT GTT GAT AAC

AGT ATT ATT ACG TCC ATC AAA GGT GGA ACA AAA GTA

ACT GTT GAA ACA ACC GAA TCT AAC GGC TGG CAC AAA

ATT ACT TAC AAC GAT GGA AAA ACT GGT TTC GTT AAC

GGT AAA TAC TTA ACT GAC AAA GCA GTA AGC ACT CCA

GTT GCA CCA ACA CAA GAA GTG AAA AAA GAA ACT ACT

ACT CAA CAA GCT GCA CCT GTT GCA GAA ACA AAA ACT

GAA GTA AAA CAA ACT ACA CAA GCA ACT ACA CCT GCG

CCT AAA GTA GCA GAA ACG AAA GAA ACT CCA GTA ATA

GAT CAA AAT GCT ACT ACA CAC GCT GTC AAA AGC GGT

GAC ACT ATT TGG GCT TTA TCC GTA AAA TAC GGT GTT

TCT GTT CAA GAC ATT ATG TCA TGG AAT AAT TTA TCT

TCT TCT TCT ATT TAT GTA GGT CAA AAG CTT GCT ATT

AAA CAA ACT GCT AAC ACA GCT ACT CCA AAA GCA GAA

GTG AAA ACG GAA GCT CCA GCA GCT GAA AAA CAA GCA

GCT CCA GTA GTT AAA GAA AAT ACT AAC ACA AAT ACT

GCT ACT ACA GAG AAA AAA GAA ACA GCA ACG CAA CAA

CAA ACA GCA CCT AAA GCA CCA ACA GAA GCT GCA AAA

CCA GCT CCT GCA CCA TCT ACA AAC ACA AAT GCT AAT

AAA ACG AAT ACA AAT ACA AAT ACA AAC AAT ACT AAT

ACA CCA TCT AAA AAT ACT AAT ACA AAC TCA AAT ACT

AAT ACG AAT ACA AAC TCA AAT ACG AAT GCT AAT CAA

GGT TCT TCC AAC AAT AAC AGC AAT TCA AGT GCA AGT

GCT ATT ATT GCT GAA GCT CAA AAA CAC CTT GGA AAA

GCT TAT TCA TGG GGT GGT AAC GGA CCA ACT ACA TTT

GAT GCC TCT GGT TAC ACT AAA TAT GTA TTT GCT AAA

GCG GGT ATC TCC CTT CCA CGT ACA TCT GGC GCA CAA

TAT GCT AGC ACT ACA AGA ATT TCT GAA TCT CAA GCA

AAA CCT GGT GAT TTA GTA TTC TTC GAC TAT GGT AGC

GGA ATT TCT CAC GTT GGT ATT TAT GTT GGT AAT GGT

CAA ATG ATT AAC GCG CAA GAC AAT GGC GTT AAA TAC

GAT AAC ATC CAC GGC TCT GGC TGG GGT AAA TAT CTA

GTT GGC TTC GGT CGC GTA TAA

E415 Protein Amino Acid Sequence (SEQ ID NO:1)
T V V V E A G D T L W G I A Q S K G T T V D A I K K A N N L T T D K I V P G Q K L Q V N N E V A A A E K T E K S V S A T W L N V R T G A G V D N S I I T S I K G G T K V T V E T T E S N G W H K I T Y N D G K T G F V N G K Y L T D K A V S T P V A P T Q E V K K E T T T Q Q A A P V A E T K T E V K Q T T Q A T T P A P K V A E T K E T P V I D Q N A T T H A V K S G D T I W A L S V K Y G V S V Q D I M S W N N L S S S S I Y V G Q K L A I K Q T A N T A T P K A E V K T E A P A A E K Q A A P V V K E N T N T N T A T T E K K E T A T Q Q Q T A P K A P T E A A K P A P A P S T N T N A N K T N T N T N T N N T N T P S K N T N T N S N T N T N T N S N T N A N Q G S S N N N S N S S A S A I I A E A Q K H L G K A Y S W G G N G P T T F D A S G Y T -continued K Y V F A K A G I S L P R T S G A Q Y A S T T R I S E S Q A K P G D L V F F D Y G S
G I S H I G I Y V G N G Q M I N A Q D N G V K Y D N I H G S G W G K Y L V G F G R
V

| LysM1 | SH3 | LysM2 | TN | NLPC/p60 |
|---|---|---|---|---|
| Bold | Underline/Italics | Bold | Italics | Underline |

Full Length 10403s p60 with Leader Sequence (SEQ ID NO: 5)
MKKATIAATAGIAVTAFAAPTIASASTVVVEAGDTLWGIAQSKGTTVDAI
KKANNLTTDKIVPGQKLQVNNEVAAAEKTEKSVSA*TWLNVRTGAGVDNSI*
*ITSIKGGTKVTVETTESNGWHKITYNDGKTGFVNGKYLT*DKAVSTPVAPT
QEVKKETTTQQAAPVAETKTEVKQTTQATTPAPKVAETKETPVIDQNATT
HAVKSGDTIWALSVKYGVSVQDIMSWNNLSSSSIYVGQKLAIKQTANTAT
PKAEVKTEAPAAEKQAAPVVKENTNTNTATTEKKETATQQQTAPKAPTEA
*AKPAPAPSTNTNANKTNTNTNTNNTNTPSKNTNTNSNTNTNTNSNTNANQ*
*GSSNNNSNSSASAIIA*EAQKHLGKAYSWGGNGPTTFDCSGYTKYVFAKAG
ISLPRTSGAQYASTTRISESQAKPGDLVFFDYGSGISHVGIYVGNGQMIN
AQDNGVKYDNIHGSGWGKYLVGFGRV In some embodiments, a peptide composition can include a peptide having LysM1 AA:26-69 (1$^{st}$ spacer 15 amino acids) SH3 AA:86-139 (2$^{nd}$ spacer 58AA) LysM2 AA:199-243 NLPC AA:373-476. Other embodiments include peptide compositions including a peptide having LysM1 aa26-69 (1st spacer 15 aa) SH3 aa86-139 (2nd spacer 58aa). It is contemplated that a peptide may include a peptide 80 percent or more homologous to peptides disclosed herein that are capable of inducing NK cell activation. Alternatively a peptide contemplated herein can include a peptide having the following motif:

xxxxxxGDTxWxxxKxxxxxxxxxxxNNLxxxxxxxVxGQKLxx of SEQ ID NO: 12.

Full E41.5 (p60$^{c389A}$)

(SEQ ID NO: 6)
MKKATIAATAGIAVTAFAAPTIASASTVVVEAGDTLWGIAQSKGTTVDAI
KKANNLTTDKIVPGQKLQVNNEVAAAEKTEKSVSA*TWLNVRTGAGVDNSI*
*ITSIKGGTKVTVETTESNGWHKITYNDGKTGFVNGKYLT*DKAVSTPVAPT
QEVKKETTTQQAAPVAETKTEVKQTTQATTPAPKVAETKETPVIDQNATT
HAVKSGDTIWALSVKYGVSVQDIMSWNNLSSSSIYVGQKLAIKQTANTAT
PKAEVKTEAPAAEKQAAPVVKENTNTNTATTEKKETATQQQTAPKAPTEA
*AKPAPAPSTNTNANKTNTNTNTNNTNTPSKNTNTNSNTNTNTNSNTNANQ*
*GSSNNNSNSSASAIIA*EAQKHLGKAYSWGGNGPTTFDASGYTKYVFAKAG
ISLPRTSGAQYASTTRISESQAKPGDLVFFDYGSGISHVGIYVGNGQMIN
AQDNGVKYDNIHGSGWGKYLVGFGRV

Catalytic Triad Null (SEQ ID NO: 7)
MKKATIAATAGIAVTAFAAPTIASASTVVVEAGDTLWGIAQSKGTTVDAI
KKANNLTTDKIVPGQKLQVNNEVAAAEKTEKSVSA*TWLNVRTGAGVDNSI*
*ITSIKGGTKVTVETTESNGWHKITYNDGKTGFVNGKYLT*DKAVSTPVAPT
QEVKKETTTQQAAPVAETKTEVKQTTQATTPAPKVAETKETPVIDQNATT
HAVKSGDTIWALSVKYGVSVQDIMSWNNLSSSSIYVGQKLAIKQTANTAT
PKAEVKTEAPAAEKQAAPVVKENTNTNTATTEKKETATQQQTAPKAPTEA
*AKPAPAPSTNTNANKTNTNTNTNNTNTPSKNTNTNSNTNTNTNSNTNANQ*
*GSSNNNSNSSASAIIA*EAQKHLGKAYSWGGNGPTTFDASGYTKYVFAKAG
ISLPRTSGAQYASTTRISESQAKPGDLVFFDYGSGISAVGIYVGNGQMIN
AQDNGVKYDNIAGSGWGKYLVGFGRV LysM1-SH1

(SEQ ID NO: 8)
STVVVEAGDTLWGIAQSKGTTVDAIKKANNLTTDKIVPGQKLQVNNEVA
AAEKTEKSVSA*TWLNVRTGAGVDNSIITSIKGGTKVTVETTESNGWHKI*
*TYNDGKTGFVNGKYLT*

SH3-LysM2

(SEQ ID NO: 9)
*TWLNVRTGAGVDNSIITSIKGGTKVTVETTESNGWHKITYNDGKTGFVNG*
*KYLT*DKAVSTPVAPTQEVKKETTTQQAAPVAETKTEVKQTTQATTPAPKV
AETKETPVIDQNATTHAVKSGDTIWALSVKYGVSVQDIMSWNNLSSSSIY
VGQKLAIKQ

(SEQ ID NO: 10)
STVVVEAGDTLWGIAQSKGTTVDAIKKANNLTTDKIVPGQKLQV--44

LysM1

(SEQ ID NO: 11)
HAVKSGDTIWALSVKYGVSVQDIMSWNNLSSSSIYVGQKLAIKQ 44

LysM2

(SEQ ID NO: 12)
xxxxxxGDTxWxxxKxxxxxxxxxxxNNLxxxxxxxVxGQKLxx Common AAs in alignment are noted (bold).

DNA Encoding the N-Terminal Fragment of the Mature p60/E415

(SEQ ID NO: 13)
```
ACT GTA GTA GTC GAA GCT GGT GAT ACT CTT TGG GGT
ATC GCA CAA AGT AAA GGG ACT ACT GTT GAC GCA ATT
AAA AAA GCA AAC AAT TTA ACA ACA GAT AAA ATC GTA
CCA GGT CAA AAA TTA CAA GTA AAT AAT GAG GTT GCT
GCT GCT GAA AAA ACA GAG AAA TCT GTT AGC GCA ACT
TGG TTA AAC GTC CGT ACT GGC GCT GGT GTT GAT AAC
AGT ATT ATT ACG TCC ATC AAA GGT GGA ACA AAA GTA
ACT GTT GAA ACA ACC GAA TCT AAC GGC TGG CAC AAA
ATT ACT TAC AAC GAT GGA AAA ACT GGT TTC GTT AAC
GGT AAA TAC TTA ACT GAC AAA GCA GTA AGC ACT CCA
GTT GCA CCA ACA CAA GAA GTG AAA AAA GAA ACT ACT
ACT CAA CAA GCT GCA CCT GTT GCA GAA ACA AAA ACT
GAA GTA AAA CAA ACT ACA CAA GCA ACT ACA CCT GCG
CCT AAA GTA GCA GAA ACG AAA GAA ACT CCA GTA ATA
GAT CAA AAT GCT ACT ACA CAC GCT GTC AAA AGC GGT
GAC ACT ATT TGG GCT TTA TCC GTA AAA TAC GGT GTT
TCT GTT CAA GAC ATT ATG TCA TGG AAT AAT TTA TCT
TCT TCT TCT ATT TAT GTA GGT CAA AAG CTT GCT ATT
AAA CAA ACT GCT AAC ACA GCT ACT CCA AAA GCA GAA
GTG AAA ACG GAA GCT CCA GCA GCT GAA AAA CAA GCA
GCT CCA GTA GTT AAA GAA AAT ACT AAC ACA AAT ACT
GCT ACT ACA GAG AAA AAA GAA ACA GCA ACG CAA CAA
CAA ACA GCA CCT AAA GCA CCA ACA GAA GCT GCA AAA
CCA GCT CCT GCA CCA TCT ACA AAC
```

N-Terminal Fragment p60 Amino Acid Sequence (SEQ ID NO: 14)
```
T V V V E A G D T L W G I A Q S K G T T V D A I K
K A N N L T T D K M I V P G Q K L Q V N N E V A A
A E K T E K S V S A T W L N V R T G A G V D N S I
I T S I K G G T K V T V E T T E S N G W H K I T Y
N D G K T G F V N G K Y L T D K A V S T P V A P T
Q E V K K E T T T Q Q A A P V A E T K T E V K Q T
T Q A T T P A P K V A E T K E T P V I D Q N A T T
H A V K S G D T I W A L S V K Y G V S V Q D I M S
W N N L S S S I Y V G Q K L A I K Q T A N T A T
P K A E V K T E A P A A E K Q A A P V V K E N T N
T N T A T T E K K E T A T Q Q Q T A P K A P T E A
A K P A P A P S T N
```

DNA Sequence Encoding the C-Terminal Fragment of the Mature p60 Gene (SEQ ID NO: 15)
```
ACA AAT GCT AAT AAA ACG AAT ACA AAT ACA AAT ACA
AAC AAT ACT AAT ACA CCA TCT AAA AAT ACT AAT ACA
AAC TCA AAT ACT AAT ACG AAT ACA AAC TCA AAT ACG
AAT GCT AAT CAA GGT TCT TCC AAC AAT AAC AGC AAT
TCA AGT GCA AGT GCT ATT ATT GCT GAA GCT CAA AAA
CAC CTT GGA AAA GCT TAT TCA TGG GGT GGT AAC GGA
CCA ACT ACA TTT GAT TGC TCT GGT TAC ACT AAA TAT
GTA TTT GCT AAA GCG GGT ATC TCC CTT CCA CGT ACA
TCT GGC GCA CAA TAT GCT AGC ACT ACA AGA ATT TCT
GAA TCT CAA GCA AAA CCT GGT GAT TTA GTA TTC TTC
GAC TAT GGT AGC GGA ATT TCT CAC GTT GGT ATT TAT
GTT GGT AAT GGT CAA ATG ATT AAC GCG CAA GAC AAT
GGC GTT AAA TAC GAT AAC ATC CAC GGC TCT GGC TGG
GGT AAA TAT CTA GTT GGC TTC GGT CGC GTA TAA
```

C-Terminal Fragment p60 Amino Acid (SEQ ID NO: 16)
```
T N A N K T N T N T N T N N T N T P S K N T N T N
S N T N T N T N S N T N A N Q G S S N N N S N S S
A S A I I A E A Q K H L G K A Y S W G G N G P T T
F D C S G Y T K Y V F A K A G I S L P R T S G A Q
Y A S T T R I S E S Q A K P G D L V F F D Y G S G
I S H V G I Y V G N G Q M I N A Q D N G V K Y D N
I H G S W G K Y L V G F G R V
```

In certain embodiments, a kit contemplated herein may include one or more compositions for inducing an innate immune response in a subject. The kits may include a container means. Any of the kits will generally include at least one vial, test tube, flask, bottle, syringe or other container means, into which the testing agent, may be preferably and/or suitably aliquoted. Kits herein may also include a means for comparing the results to a suitable control sample such as a positive and/or negative control. Other components for kits of use for treating a subject having a bacterial or viral infection or other condition disclosed herein can include a peptide or mutant p60 composition. Kits may further include other agents known to treat an infection, an autoimmune disorder or cancer.

Certain subjects contemplated herein can include humans or non-human mammals.

EXAMPLES

The following examples are included to illustrate various embodiments. It should be appreciated by those of skill in the art that the techniques disclosed in the examples that follow represent techniques discovered to function well in the practice of the claimed methods, compositions and apparatus. However, those of skill in the art should, in light of the present disclosure, appreciate that many changes may be made in the specific embodiments which are disclosed and still obtain a like or similar result without departing from the spirit and scope of the invention.

Bacterial Expression of p60 Enhances IFNγ Production in DC/NK Co-Cultures

In one exemplary method, it was observed that Wildtype Lm infection induces a robust IFNγ response from NK cells in vivo, peaking around 24 hours post-infection. By contrast, it was observed that in vivo infection with an attenuated Δp60 mutant Lm elicited weak IFNγ production from NK cells despite similar bacterial numbers in infected tissues. It was confirmed that this reduction in NK cell activation was not due to defective association of Δp60-infected cells with NK cells as in vitro infection of DC/NK co-cultures with Δp60 Lm elicited a poor IFNγ response from naïve NK cells (FIG. 1A). This was true also for other independent p60 deletion mutants made in both 10403s and EGD wild type backgrounds (FIG. 1B). To confirm that p60 was responsible for the increased NK cell activation, the Δp60 mutant was complemented by expression of a His tagged p60 from the pHELP promoter of the pIMK2 vector, previously demonstrated. The complemented Δp60+p60 strain secreted p60 at levels comparable to wild-type Lm, based on immunoblots of protein Lm culture supernatants (not shown). Infection of co-cultures with the complemented Δp60+p60 strain restored IFNγ production to levels seen in wt Lm (FIG. 1C). It was then verified that bacterial expression of p60 specifically enhanced IFNγ by NK cells by staining for intracellular IFNγ in the NWNA following 10 hour co-culture (FIG. 1D). Thus, it was confirmed that Lm expression of p60 specifically increases IFNγ production by NK cells but not other cell types.

FIGS. 1A-1D represent bacterial expression of p60 enhances NK activation in co-culture. (1A) BMDCs were infected with LmWT (10403s) or the Δp60 mutant strain. NK-enriched NWNA splenocytes were added 2 hours post-infection, and co-culture supernatant was harvested 21 hours post-infection. Average IFNγ concentration is plotted; error bars represent SEM. Data are pooled from 11 independent experiments. (1B) BMDC were infected in triplicate with WT (10403s or EGD) or one of two independent Δp60 deletion mutants in each background strain. NWNA splenocytes were added to the co-culture and IFNγ levels were measured by ELISA 21 hours post infection. (1C) BMDCs were infected in triplicate with LmWT, Δp60, or Δp60 complemented with His-tagged p60. Average IFNγ concentration+/−SEM is shown. (1D) BMDC were infected with 10403s or Δp60 Lm and washed with gentamycin after 1 hour. NWNA cells were added 2 hours post-infection, and removed at 10 hours post-infection. These NWNA cells were stained for CD, NK1.1, and intracellular IFNγ. NK cells included NK1.1 positive, CD3 negative cells, and T cells include CD3 positive, NK1.1 negative cells. Average percent IFNγ positive cells+/−SEM are shown.

Bacterial Expression of p60 Correlates with Increased IL-1β and IL-18 Secretion from DCs During Infection In another exemplary method, cytokine activation and production was examined related to NK cell activation. In one example illustrated in FIG. 2A IL-12 production was examined. It was tested whether bacterial p60 expression influenced production of IL-12 by infected bone marrow derived dendritic cells (BMDCs). BMDCs are cells derived from mouse bone marrow cultured in the presence of GM-CSF cytokine Using ELISAs, the amounts of Il-12 produced and secreted were measured following infection with wt or Δp60 Lm. No significant difference in the levels of secreted Il-12 was observed (FIG. 2A). Then, production of IL-18 was assessed, an important cytokine for IFNγ production. IL-18−/− BMDCs elicited little NK cell IFNγ production in response to Lm infection (FIG. 2B). Additionally, there was no difference in the residual IFNγ produced in response to infection by wt versus Δp60 Lm. By contrast, IL-10 and IL-18 was detected in supernatants of wt C57BL/6 DCs infected with wt Lm. However, secretion of both cytokines was significantly reduced in DCs infected with Δp60 Lm (FIGS. 2C and 2D). Secreted IL-1β and IL-18 are processed by one of several caspase-1 inflammasomes prior to secretion. Consistent with defective inflammasome activation, it was also observed that very little processed IL-1β was found in lysates from DC infected with Δp60 Lm (FIG. 2E). These findings indicated that infection of DC by bacteria lacking p60 likely leads to reduced activation of the caspase-1 inflammasome and correspondingly reduced production of the NK cell activating cytokine IL-18.

FIGS. 2A-2E represent bacterial production of p60 enhances IL-10 and IL-18 secretion, leading to robust NK activation. All treatments were performed in triplicate; average concentrations+/−SEM are shown. (2A) BMDC were infected with 10403s or Δp60 *Listeria*. 21 hours post stimulation, the supernatant was assessed for IL-12. (2B) BMDC from C57B6 or IL-18$^{-/-}$ mice were infected with 10403s or Δp60 *Listeria* as previously. NWNA splenocytes were added 2 hours post infection, and INFγ secretion was measured by ELISA 21 hours post-infection. (2C and 2D) BMDC were infected as in (A) and supernatant levels of IL-18 (2C) and IL-1β (2D) were measured by ELISA. (2E) 2 million BMDC were infected for 21 hours and the lysates were probed for IL-1β cleavage.

FIG. 3 represents that LPS priming can restore IFNγ-inducing activity to detoxified His-p60 but not ATP stimulation. Dendritic cells were treated with Mug of His-p60 pre- or post-polymyxin B detoxification, 5 mM ATP, or Lm WT MOI 1. Cells were given either no pretreatment or treated for 3 hours prior to infection with crude LPS at 50 ng/ml. NK cells were added 2 hours post-infection. IFNγ levels (3A) or IL-10 levels (3B) were measured by ELISA 21 hours post-treatment.

Δp60 Lm are not Growth Deficient in BMDC

In another example, it was examined whether reduced inflammasome and NK cell activation in response to Δp60 infection might reflect reductions in bacterial burdens within the infected DCs. Thus, infections by wt and Δp60 mutant Lm were compared. It was observed that only a 4-fold increase in CFUs of both wt and Δp60 Lm strains from 4 to 12 hours post-infection (data not shown), which is consistent with prior work indicating that DCs are poorly permissive to Lm infection. The average number of bacteria per cell was similar for WT and Δp60 Lm over the infection time-course (data not shown), as was the percent infected cells (data not shown). Furthermore, there was no difference in the ratio of cytosolic versus phagosomal localized Lm between the two strains (data not shown). Together, these data indicated that p60 was not required for the invasion and multiplication of Lm in DCs. Therefore, it is likely that the reduced caspase-1 activation was not due to defective growth of the Δp60 strain.

Purified p60 can Activate NK Cells in Co-Culture with TLR Stimulation

Based on the data obtained, a role for p60 in activation of the inflammasome during Lm infection was investigated in another exemplary experiment. Thus, whether purified recombinant p60 protein might be sufficient for triggering the inflammasome in DCs and hence promote NK cell IFNγ production was examined. A recombinant His-tagged p60 was expressed and purified from E. coli using nickel affinity and cation exchange columns. It was observed that the purified p60 was able to induce IFNγ in DC/NK co-culture (FIG. 4A). However, an issue with this result was that p60 protein purified from E. coli might be contaminated with LPS. The initial preparation of purified p60 protein contained ~10 ng of LPS per 10 ug of protein. This LPS contamination was not likely responsible for NK cell activation, however, as 10 ng of LPS was not by itself sufficient to stimulate IFNγ production. Furthermore, neither BSA nor a phage autolysin (HPL511) purified from E. coli and contaminated with ~10 ng LPS were sufficient to activate NK cells in this system (FIG. 4A).

To further exclude possible artifacts due to LPS polymyxin B columns were used to remove LPS from the purified p60 protein. Initially, it was found that detoxified p60 was insufficient to activate NK cell IFNγ production (FIG. 4B). Whether DC activation or maturation state might affect the efficacy of p60 stimulation was examined. A three hour pre-stimulation was tested to see whether TLR agonist might prime the DCs and/or NK cells to subsequently respond to p60 stimulation. These results illustrated that pre-stimulation with LPS or the non-toxic LPS analog monophosphoryl LipidA (MPA) or poly I:C (PI:C) sufficed to elicit IFNγ production following p60 stimulation (FIG. 4B). As with Lm infection (FIG. 1D), NK cells were found to be the source of IFNγ produced in p60-stimulated co-cultures (FIG. 4C).

TLR stimulation elicits production of inflammatory cytokines that might alter DC activation and/or provide additional stimulation to NK cells. For example, IL-12 strongly enhances IFNγ induction in NK cells. It was observed that detoxified p60 failed to induce significant levels of IL-12, whereas both PI:C and MPA were sufficient to elicit IL-12 production in NK/BMDC co-cultures (FIG. 4D). Next, whether production of IL-12 or other inflammatory cytokines such as TNFα and IFNβ might be responsible for the priming effects of TLR stimuli were investigated (FIG. 4E). It was observed that none of these cytokines induced IFNγ from NK cells on their own. However, IL-12, IFNβ, and TNFα each primed the co-cultures to produce IFNγ after treatment with detoxified p60. IL-12 appeared to be the most potent priming agent, likely due to the reported enhancement of IFNγ transcription in NK cells. Together, these experiments revealed that in the presence of TLR agonists or recombinant cytokines, recombinant p60 protein was sufficient to activate mouse NK cells. Due to the enhanced NK cell activation in the presence of DCs treated with TLR agonists or recombinant cytokines, some treatment applications leading to DC and/or NK cell activation may, depending on the circumstances, require TLR/cytokine stimulation in combination with p60, p60 protein derived mutants or peptides to achieve optimal stimulation.

FIGS. 4A-4E represent purified p60 can activate NK cells in co-culture with TLR stimulation. All treatments were performed in triplicate; average cytokine levels+/−SEM are shown. (4A) NWNA cells were co-cultured with BMDC infected with LmWT or treated with 10 ug of recombinant his-tagged p60 purified from E. coli, 10 ng LPS, 10 ug BSA, or 10 ug of his-tagged phage autolysin HPL511. (4B) Purified p60 was detoxified via polymyxin B column to remove LPS. BMDC were primed for 3 hours with 20 ug/ml poly I:C, 10 ng/ml LPS, or 10 ng/ml MPA, and then treated with 10 ug of detoxified protein. NWNA splenocytes were co-cultured two hours post-infection, and IFNγ was measured by ELISA 21 hours post-infection. (4C) BMDC were pretreated with 20 ug/ml poly I:C for 3 hours before being stimulated with 10 ug detoxified p60. 2 hours post-p60 treatment, 1 million NWNA cells were co-cultured with the BMDC. 10 hours post-p60 treatment, the NWNA were collected and stained for CD3, NK1.1, and IFNγ. NK cells are NK1.1 positive, CD3 negative, while T cells are CD positive, NK1.1 negative. The average percent positive IFNγ cells are shown +/−SEM. (4D) Supernatants from BMDC and NWNA co-culture as in (B) were analyzed for IL-12 secretion by ELISA. (4E) BMDC were treated with 2 ng IL-12, 100 units IFNβ, or 2 ng TNFα with or without 10 ug detoxified p60. NWNA cells were added 2 hours post-treatment, and IFNγ levels were measured by ELISA 21 hours post-stimulation.

TLR and p60 Stimulation Induces NLRP3-Dependent Inflammasome Activation

Experiments using Δp60 Lm suggested that p60 expression enhances inflammasome activation in DCs. So, whether addition of purified p60 might elicit inflammasome activation and secretion of active IL-1β and IL-18 from BMDCs was examined. Detoxified p60 in combination with TLR stimulation increased secreted IL-1β and IL-18 (FIG. 5A-D). Absence of IL-18 in IL-18$^{-/-}$ DCs demonstrated that NK cells produced very little IFNγ in response to p60. It was then found that DCs from NLRP3$^{-/-}$ mice were unable to activate NK cells in response to p60 stimulation. Taken together, it was observed that p60 protein stimulates the NLRP3 inflammasome to produce IL-18 (FIG. 5E).

FIGS. 5A-5E represent TLR and p60 stimulation induce NRLP3-dependent inflammasome activation required for NK activation in co-culture. All treatments were performed in triplicate; average IFNγ levels+/−SEM are shown. BMDC were treated with 20 ug/ml poly I:C for three hours and then stimulated with 10 ug detoxified p60. IL-1β (5A) or IL-18 (5B) in the supernatant was measured by ELISA. Average cytokine levels+/−SEM are shown. (5C) Cell lysates from 2 million BMDC were assayed by western blot for IL-β and IL-18 production and cleavage. (5D) BMDC were primed for 3 hours with 20 ug/ml poly I:C or 10 ng/ml MPA and stimulated with 10 ug detoxified p60. IL-18 levels were measured 21 hours post-treatment (5E) BMDC from C57B6, NLRP3$^{-/-}$, or IL-18$^{-/-}$ mice were primed with 20 ug/ml poly I:C or 10 ng/ml MPA and stimulated with Mug detoxified p60. NWNA were added 2 hours post-stimulation, and IFNγ was measured by ELISA 21 hours post stimulation.

The Enzymatic Domain of p60 is not Required for DC/NK Activation

The p60 protein sequence consists of an N-terminal portion containing two LysM domains separated by an SH3 domain, and a C-terminal repeat region followed by a single NLPC/p60 domain. This NLPC/p60 domain is the proposed catalytic domain. Due to its homology with the Bacillius subtilis LytF endopeptidase, p60 is thus predicted to cleave the peptide cross-linking bridge of peptidoglycan. However, previously presented results revealed that purified recombinant p60 was able to stimulate DC/NK co-cultures in the absence of Listeria PGN. Therefore, whether the enzymatic domain of p60 was necessary for p60 stimulatory activity was examined. Guided by the conserved active sites of the NLPC/p60 family, a putative catalytic triad was identified in p60, consisting of cysteine residue 389 and histidine residues 439 and 465 (FIG. 6A). Using site-directed mutagenesis, C389 was mutated to alanine (referred to as p60$^{C389A}$ mutant). The p60$^{C389A}$ mutant was then cloned into the pTrc-His TOPO vector (Invitrogen) for His-tagged protein expression. Purified wt his-p60 was weakly active on heat-killed Lm and crude Lm PGN substrates, as assessed by zymography (FIG. 6B). In contrast, p60$^{C389A}$ failed to show any cleavage of the PGN substrate (FIG. 6B). However, purified p60$^{C389A}$ still induced NK activation in co-culture as efficiently as catalytically active protein (FIG. 6C). These data revealed that the enzymatic activity of p60 was not required for its activity, for example, its ability to stimulate DCs to activate NK cells.

FIGS. 6A-6C represent that p60 enzymatic activity is not required for NK stimulation in co-culture. (6A) p60 domain map where the p60 protein consists of two LysM domains on either side of an SH3 domain in the N terminal portion. The C-terminus consists of an NLPC/p60 domain preceded by a TN repeat region. C389, H439 and H 465 are the predicted catalytic triad. (6B) 10 ug each of p60, p60$^{C389A}$, and 0.25 ug of phage autolysin HPL511 were loaded into native heat-killed Lm PAGE gels. After renaturation and overnight incubation, zymography activity was visualized by staining with methylene blue. The image was inverted using Adobe Photoshop®. P60 shows weak PGN hydrolase activity compared to the phage autolysin. p60$^{C389A}$ is catalytically inactive. In native zymography gels, p60 activity appears around 150 kD. (6B) BMDC were treated with 10 ng LPS, with or without 10 ug detoxified p60 protein, or p60 protein with the C389A catalytic domain mutation. (6C) BMDC were treated in triplicate with 10 ng/ml MP A or 20 ug/ml poly 1:C for 3 hours before being stimulated with 10 ug/ml detoxified protein. NWNA were added 2 hours post infection, and IFNγ was measured by ELISA 21 hours post infection. Average IFNγ levels+/−SEM are shown.

In another exemplary experiment, regions of the p60 protein were mapped out that are important for its ability to stimulate the DC/NK co-culture. First, p60 was separated into two truncated proteins. The N-terminal fragment of the protein (Np60) was truncated immediately before the TN repeat region, while the C-terminal fragment (C-p60) included the TN repeats and NLPC/p60 domain. These truncated proteins were cloned and expressed using the pTrcHis system. (FIGS. 7 A and 7B) The underlined residues are the consensus for this domain. Bold residues appear to be more specific for the p60 LysM1 domain and may contribute to specific functions of this domain. The proteins or peptides were purified and detoxified as with full length p60. The fragments were then tested for DC/NK stimulation activity with either poly I:C or MPA acting as TLR pre-stimulation (FIG. 7C). Np60 induced IFNγ production in co-cultures pre-stimulated with either PI:C or MP A, while Cp60 did not substantially induce IFNγ in the co-cultures. To further map the necessary region for DC stimulation, his-tagged fragments were constructed consisting of the first LysM domain plus the SH3 domain, a fragment including the SH3 domain plus the second LysM2 domain, and a fragment including the second LysM domain alone. These three fragments of the N-terminal portion of the protein were assayed for activity in the DC/NK co-culture. (FIG. 7C) The fragment including the first LysM and SH3 domains was sufficient to stimulate the DCs to induce TFNγ production from the NK cells, while the SH3-LysM2 and LysM2 alone fragments did not appear to induce significant IFNγ production in these examples. These experiments may be repeated for further analysis.

FIGS. 7A-7C represents the LysM1-SH3 region of p60 is sufficient to stimulate DC/NK co-cultures and that enzymatic activity is not required for NK cell activation, FIG. 7D. FIGS. 7A and B represent that p60 domain map illustrated that the p60 protein consists of two LysM domains on either side of an SH3 domain in the N terminal portion. The C-terminus consists of an NLPC/p60 domain preceded by a TN repeat region. Np60 is truncated immediately preceding the TN repeat domain. Cp60 consists of the TN repeat region and the NLPC/p60 catalytic domain. (7C) BMDC were treated in triplicate with 10 ng/ml MPA or 20 ug/ml poly 1:C for 3 hours before being stimulated with 10 ug/ml detoxified Np60, Cp60, or full-length p60. NWNA were added 2 hours post infection, and IFNγ was measured by ELISA 21 hours post infection. Average IFNγ levels+/−SEM are shown. (7C) BMDC were treated in triplicated with 20 ug/ml poly I:C for 3 hours before being stimulated with 10 ug/ml detoxified LysM1+SH3, SH3+LysM2, or LysM2 protein. NWNA were added 2 hours post infection, and IFNγ was measured by ELISA 21 hours post infection. Average IFNγ levels+/−SEM are shown.

p60 With IL-12 can Stimulate Human DC/PBMC Co-Cultures

Having shown that p60 in combination with inflammatory cytokines or TLR stimulation can enhance DC activation of naïve mouse NK cells, whether similar approaches might be useful for manipulating human NK cell activation was examined. Interaction between p60 protein, DCs and NK cells was analyzed in a human system. As with the murine co-cultures, it was observed that the combination of IL-12 and p60$^{C389A}$ protein induced significant IFNγ production from the co-culture, while neither the IL-12 or detoxified protein alone stimulated the response (FIG. 8).

FIG. 8 represents that human DC/NK co-cultures produce IFNγ in response to p60 and IL-12. Human PBMCs were cultured with GM-CSF and IL-4 to form DCs. Human DCs were plated in triplicate and treated the next day with 10 ug of detoxified p60$^{C389A}$ alone or in combination with 2 ng/ml hIL-12. NK cells from the same donor were added 2 hours post-treatment. Supernatants were analyzed for IFNγ using ELISA 21 hours post treatment.

In another embodiment, p60 derived peptides and mutants (e.g. E415) can be used to determine their ability to improve the outcome of mice challenged with an NK cell sensitive tumor. The ability of NK cells to promote clearance of transplanted mouse tumors and impede development of spontaneous tumors has been previously established. A tumor model used in many of these studies is the B16 melanoma, which is implanted under the skin of mice. Tumor diameter is measured using calipers and the area of the tumor is calculated for each mouse. Another quantifiable tumor model is the use of GFP-tagged B cell lymphoma cells from Myc-transgenic mice (TBL12 cells). Recent studies demonstrated that infection of tumor-bearing mice with *L. monocytogenes* activates NK cells and induces clearance of TBL12 cells from lymphoid organs. One protocol for these experiments is to inject the tumor cells 10 days prior to infection, thus inducing the rejection of an established tumor. Consistent with this interpretation, mice treated with whole bacteria survive significantly longer than untreated tumor-bearing mice. Whether NK cell activation using the peptide or mutant treatment regimen developed above reduces tumor burden using the TBL12 model will be tested. This is relevant to haematological cancer. However, it is not yet formally known if TBL12 is susceptible to clearance by NK cells. In addition, the experiment may be repeated with an established B16 model.

Figure 9:
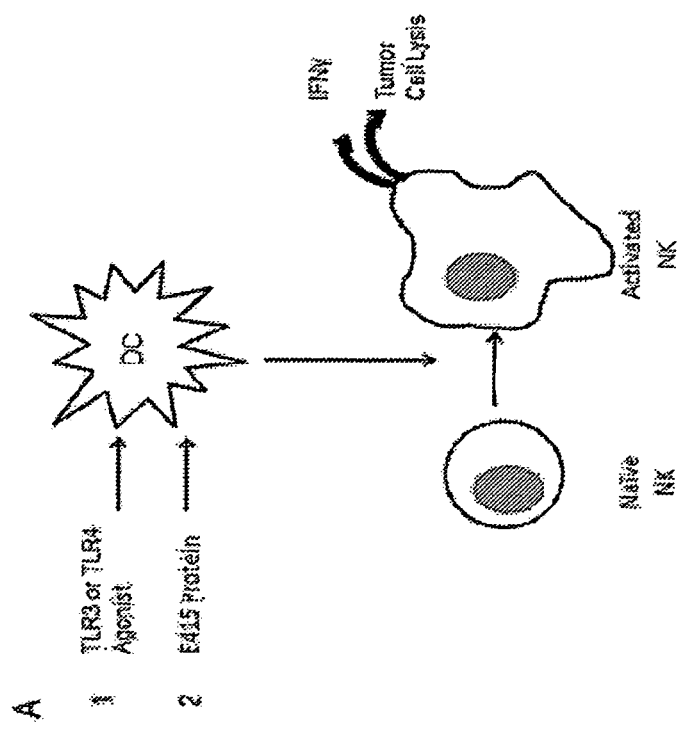
FIG. 9 represents a schematic of NK cell activation.

Studies revealed that priming of naïve NK cells may occur prior to their activation by E415 (FIG. 9). In certain examples, LPS and poly I:C (pIC) both work as priming agents in experiments (FIG. 9 and not shown), but may not, by themselves be sufficient to activate naïve NK cells. Thus, E415 may require priming to activate naïve NK cells following in vivo treatment. Therefore, one cohort of mice will also be treated pIC, an agent long used for in vivo priming of mouse NK cells. One treatment regimen, based on dose of E415 and use of pIC or not, will be determined and performed experimentally. In one exemplary experiment, administration of 300 ug of purified E415 delivered via intraperitoneal (i.p.) injection resulted in an increase of IFNγ-positive NK cells prepared from splenocytes and peritoneal lavage (data not shown). It was demonstrated that secreted serum levels IFNγ and IL-10 increased upon treatment with the purified E415 (FIG. 10).

FIG. 10 represents that i.p. administration of purified E415 can induce IFNγ and IL-10 secretion in vivo. Mice were injected i.p. with 300 ug E415, or 0.6 ug LPS, or 1×10$^4$ CFU wt Lm. Serum was collected 24 hours post treatment and assessed for IFNγ (10A) or IL-10 (10B) levels by ELISA.

In another exemplary method concerning an animal model, recombinant E415 protein can be isolated and delivered to mice at doses of about 10, 50, and 300 µg/animal via i.p. injection. These doses of E415 are based in part on observations that about 10-30 µg/ml of E415 protein is sufficient to activate NK cells in culture and the volume of a 6 week old mouse is about 20 ml. In addition, in other studies biological effects undertaken are seen when administering antibodies in this range of concentrations. NK cell activation can be measured in the spleens of injected animals at 24 h after injection using flow cytometry and scrum ELISA to quantify IFNγ production, as previously published and incorporated herein by reference in its entirety. Previous literature indicates that NK cells should be "primed" by cytokines prior to becoming permissive for activation. These experiments can be performed with and without exogenously administered cytokines in order to investigate this.

Materials and Methods

Mice

C57BL/6 and IL-18$^{-/-}$ mice were obtained from Jackson labs and maintained. Bone marrow from NLRP3$^{-/-}$ mice was generously provided.

Bacterial Strains

The wild type *Listeria monocytogenes* used in these studies was 10403s, except where the EGDe strain was used for comparison. In-frame deletion of p60 in 10403s and EGDe was done by allelic exchange, as previously described. The p60 complementation mutant expresses a secreted His-tagged p60 protein expressed from the pPL2-derived vector pIMK2, was provided. The following primers were used in SOE PCR to construct the protein construct: P60 for pIMK2 SOE primers BamHI, XhoI, His tag

```
                                            (SEQ ID NO: 17)
A: 5' AG GGATCC ATG AAA AAG CAA CTA TCG CGG CTA CA (SEQ ID NO: 18)
B: 5' ATG ATG ATG GTG ATG GTG ATG GTG ATG GCT TGC
GGA TGC GAT TGT TGG
```

```
                                            (SEQ ID NO: 19)
C: 5' AGC CAT CAC CAT CAC CAT CAC GTA GTC GAA GCT
GGT ACT CTT (SEQ ID NO: 20)
D: 5' AG CTCGAG TAT ACC GCA CCG AAG CCA ACT AGA
TAT TTA CC
```

94 C 1 min, 57 C 45 s, 68 C 1.5 min, 30 cycles

10403s Δp60 was transformed with the his-p60 construct and p60 protein secretion was assayed by trichloroacetic acid precipitation of supernatants from overnight Lm cultures. Immunoblots revealed that the complemented p60 mutant expressed p60 at levels comparable to the wt 10403s Lm.

Lm Growth Curves in BMDC.

To compare growth for wt versus Δp60 Lm in BMDC, ~2×10$^6$ BMDC per infection were plated in triplicate in wells of a 24-well plate containing replicate coverslips. The coverslips were collected at the indicated times post-infection and analyzed for CFU (lysis in %02 IGEPAL®) or stained with DIFCO® rabbit anti-*Listeria* O (previously described) and Fab (ab')2 goat-anti-rabbit Cy3 (Zymed®). Actin was visualized with Alexa Fluor® 488 phalloidin and nuclei were stained with DAPI (Invitrogen™, Molecular Probes®). To assess the stained cells, 150-200 cells per treatment time point were counted. *Listeria* associated with actin comets were counted as cytosolic, while *Listeria* lacking actin comets were considered phagosomal. Data are representative of 3 experiments.

Protein Purification

To purify p60 and p60$^{C389A}$, sequences for the mature proteins were cloned into the pTrcHis-TOPO TA cloning vector (Invitrogen™) and expressed in Top 10 *E. coli* using the following primers: P60

```
L3751 F:
                                            (SEQ ID NO: 21)
5' ACTGTAGTAGTCGAAGCTGGTGATACTCTT

L3752 R:
                                            (SEQ ID NO: 22)
5' AAG AGT ATC ACC AGC TTC GAC TAC TAC AGT
```

The p60$^{C389A}$ construct was made using site-directed mutagenesis with the QuikChange™ II XL SiteDirected Mutagenesis kit (Stratagene™) and the following primers:

```
                                            (SEQ ID NO: 23)
SMP27-F    CCAACTCCATTTGATGCTTCTGGTTACACTAAATATG (SEQ ID NO: 24)
SMP28-R    CATATTTAGTGTAACCAGAAGCATCAAATGTAGTTGG
```

The phage autolysin HPL511 was purified from a construct supplied by M. Loessner (Zurich). After protein expression the *E. coli* pellets were lysed with BugBuster® (Novagen™) in 20 mM Na phosphate, 0.5M NaCl, and 20 mM imidazole, pH 7.4, containing protease inhibitor and 2 mg/ml lysozyme. The proteins were purified using His-Trap® FF 5 ml affinity columns (GE) on an AKTA® FPLC (GE). When necessary, the his-tagged proteins were further purified using HI-TRAP® FF or HP (GE) cationic exchange in 50 mM HEPES buffer. LPS was removed from the proteins using Endotoxin Removing Columns (Thermo Scientific™).

BMDC Culture and Infection

For BMDC culture, femoral bone marrow was flushed and cultured with RPMI 1640 (high glucose) supplemented with 10% FBS, 1% betamercapto-ethanol, 1% Lglutamine, 1% sodium pyruvate, 1% penicillin/streptomycin, and 2 ng/ml GM-CSF. The BMDC were washed on days 2 and 4, and were harvested on day 7 and plated for >12 hours in antibiotic-free media for infection. 10403s wt or Δp60 Lm were grown to log phase and then used to infect BMDC at MOI of 1 for one hour, after which point the Lm were washed away and the cells were treated with 10 ug/ml gentamycin. For protein stimulation, $3\times10^5$ cells were treated with 10 ug purified protein, with or without a pre-treatment of 10 ng/ml ultra-pure LPS, 10 ng/ml mono-phosporo-Lipid A (MPA) (Sigma-AlderichSIGMA-ALDRICH®), or 20 ug/ml Polyinosine-polycytidylic acid (PI:C) (Invivogen®) for three hours.

NK Co-Culture

Splenocytes were prepared and enriched for lymphoctyes as described (Humann, 2010). The lymphocytes were 5-6% NK cells based on staining with NK 1.1 (PK136) and CD3 (145-2C11) (BD BIOSCIENCES AND eBIOSCIENCE). The splenocytes were added to the BMDC at a 0.1:1 ratio at 2 hours post-infection.

Splenocyte Staining

The NK-enriched splenocytes were collected from the co-culture 10 hours post infection and cultured with GOLGIPLUG (BD BIOSCIENCES) for three hours. The samples were permeablized with saponin buffer, stained with NK 1.1 (PK136), CD3 (145-2C11), and miFNg (XMG1.2) (BD BIOSCIENCES AND eBIOSCIENCE), and fixed with paraformaldehyde buffer. Each treatment was tested in triplicate, and the data shown are representative of 3 experiments. Samples were analyzed by flow cytometery on the LSRII (BD BIOSCIENCES).

ELISAs and Western Blotting

Cytokine levels of murine IFNγ, IL-1 p, IL-12, IL-18, and human IFNγ were measured by ELISA kit (BD BIOSCIENCES, MBL INTERNATIONAL, Woburn, Mass.) in co-culture supernatant, 21 hours post-infection. To measure IL-1P and IL-18 by western blot, cell lysatcs from $2\times10^6$ BMDC per treatment were probed with goat anti-miL-1P (R&D SYSTEMS) or biotin-rat anti-IL-18 (93-10C) (MBL INTERNATIONAL) and HRP-conjugated rabbit anti-goat (Abcam) or streptavadin (BIOSCIENCES).

Human Cell DC/NK Co-Culture

PBMCs were cultured as previously described. Briefly, $5\times10^7$ PBMCs (SERACARE®) were allowed to adhere to cell culture plates for 4 hours, then washed away. The adherent cells were cultured in media containing 200 U/ml hIL-4 (R&D Systems™) and 100 U/ml hGM-CSF (R&D Systems™). The GM-CSF was refreshed on culture day 3. On culture day 5, non-adherent DCs were collected and plated in 24-well plates with $3\times10^5$ cells per well and allowed to adhere overnight. The next day, the cells were treated with 2 ng/ml hIL-12 (R&D Systems™) and 10 ug detoxified $p60^{C389A}$, alone or in combination. 2 hours post treatment, $6.2\times10^5$ PBMCs from the same donor (SERACARE®) were added per well. 21 hours post-treatment, the co-culture supernatants were harvested and assessed for hIFNγ.

Statistics

Statistic analysis was performed using GraphPad™ Prism-5. P values were assessed using unpaired t tests. In the figures, * denotes p values between 0.05 and 0.01,  denotes p values between 0.01 and 0.001, and * denotes p value s< or =0.001.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

---

What is claimed is:

1. A peptide comprising an amino acid sequence comprising at least one lysin motif (LysM) domain represented by SEQ ID NO:12, and a Src homology 3 (SH3) domain represented by SEQ ID NO:26, wherein one of the at least one LysM domains represented by SEQ ID NO:12 is 15 amino acids upstream from the SH3 domain represented by SEQ ID NO:26, wherein the peptide is capable of inducing an immune response.

2. The peptide of claim 1, further comprising an additional LysM domain represented by SEQ ID NO:12, wherein the second LysM domain is 58 amino acids downstream of the SH3 domain represented by SEQ ID NO:26.

3. The peptide of claim 2, wherein the 58 amino acids separating the SH3 domain represented by SEQ ID NO:26 and the LysM domain represented by SEQ ID NO:12 comprise an amino acid sequence, wherein the 58 amino acid sequences separating the LysM domain and the SH3 domain is not present in SEQ ID NO:1.

4. The peptide of claim 1, further comprising an additional LysM domain represented by SEQ ID NO:28 wherein the second LysM domain is 58 amino acids downstream of the SH3 domain represented by SEQ ID NO:26.

5. The peptide of claim 1, wherein the 15 amino acids separating the LysM domain represented by SEQ ID NO:12 and the SH3 domain represented by SEQ ID NO:26 comprise an amino acid sequence wherein the 15 amino acid sequence separating the LysM domain and the SH3 domain is not present in SEQ ID NO:1.

6. The peptide of claim 1, wherein the LysM domain represented by SEQ ID NO:12 and the SH3 domain represented by SEQ ID NO:26 comprise amino acid sequences not present in SEQ ID NO:1.

7. A peptide comprising an amino acid sequence comprising at least one LysM domain represented by SEQ ID NO:28, and an SH3 domain represented by SEQ ID NO:26, wherein one of the at least one LysM domains represented by SEQ ID NO:28 is at least 15 amino acids upstream from the SH3 domain represented by SEQ ID NO:26, wherein the peptide is capable of inducing an immune response.

8. The peptide of claim 7, further comprising an additional LysM domain represented by SEQ ID NO:28, wherein the second LysM domain is 58 amino acids downstream of the SH3 domain represented by SEQ ID NO:26.

9. The peptide of claim 8, wherein the 58 amino acids separating the SH3 domain represented by SEQ ID NO:26 and the LysM domain represented by SEQ ID NO:28 comprise an amino acid sequence, wherein the 58 amino acid sequence separating the LysM domain and the SH3 domain is not present in SEQ ID NO:1.

10. The peptide of claim 7, further comprising an additional LysM domain represented by SEQ ID NO:12, wherein the second LysM domain is 58 amino acids downstream of the SH3 domain represented by SEQ ID NO:26.

11. The peptide of claim 7, wherein the 15 amino acids separating the LysM domain represented by SEQ ID NO:28 and the SH3 domain represented by SEQ ID NO:26 comprise an amino acid sequence, wherein the 15 amino acid sequence separating the LysM domain and the SH3 domain is not present in SEQ ID NO:1.

12. The peptide of claim 7, wherein the LysM domain represented by SEQ ID NO:28 and the SH3 domain represented by SEQ ID NO:26 comprise amino acid sequences not present in SEQ ID NO:1.

13. A pharmaceutical composition comprising one or more peptides of claim 1, or one or more peptides of claim 7, and a pharmaceutically acceptable excipient.

14. The composition of claim 13, further comprising one or more immunoregulatory cytokines selected from the group consisting of interferon gamma (IFNγ), interleukin (IL)-18, IL-1β, IL-10, tumor necrosis factor (TNF) α, IFNα/β, IL-1α, IL-6, leukemia inhibitory factor (LIF), oncostatin M (OSM), ciliary neurotrophic factor (CTNF), transforming growth factor (TGF)-β, granulocyte macrophage-colony stimulating factor (GM-CSF), IL-11, IL-12, IL-15, IL-23, IL-28, IL-33, IL-8, IL-2, musculoaponeurotic fibrosarcoma (MAF), macrophage migration inhibitory factor (MMIF), macrophage chemotactic factor (MCF), leukocyte migration inhibitory factor (LMIF), histamine releasing factor (HRF), granulocyte colony-stimulating factor (G-CSF), macrophage colony-stimulating factor (M-CSF), chemokine (C-C motif) ligand 3 (CCL3), chemokine (C-C motif) ligand 4 (CCL4), chemokine (C-C motif) ligand 5 (CCL5), chemokine (C-X-C motif) ligand 10 (CCL10), chemokine (C-X-C motif) ligand 11 (CCL 11), and chemokine (C-X-C motif) ligand 12 (CCL12).

15. The composition of claim 13, further comprising one or more of polyinosinic:polycytidylic acid (PI:C), monophosphoryl lipid A, Pam3CSK4, Flagellin, macrophage-activating lipopeptide (MALP-2), Imiquimod, Imidazoquinoline, Resiquimod, CpG DNA, single-stranded ribonucleic acids (ssRNA), Zymosan, poly A:T, gardiquimond, hylauronic acid fragments, Kdo-2 Lipid A, and Loxoribine.

16. The composition of claim 15, further comprising one or more of interleukin-12 (IL-12), interleukin-18 (IL-18), tumor necrosis factor α (TNFα), interferon α/β (IFN α/β), interleukin-1α (IL-1α), interleukin-1β (IL-1β), interleukin-6 (IL-6), leukemia inhibitory factor (LIF), oncostatin M (OSM), ciliary neurotrophic factor (CTNF), transforming growth factor β (TGF-β), granulocyte macrophage colony-stimulating factor (GM-CSF), interleukin-10 (IL-10), interleukin-11 (IL-11), interleukin-12 (IL-12), interleukin-15 (IL-15), interleukin-23 (IL-23), interleukin-28 (IL-28), interleukin-8 (IL-8), interleukin-2 (IL-2), musculoaponeurotic fibrosarcoma oncogene (MAF), macrophage migration inhibitory factor (MMIF), macrophage chemotactic factor (MCF), leukocyte migration inhibitory factor (LMIF), histamine-releasing factors (HRF), granulocyte colony-stimulating factor (G-CSF), and macrophage colony-stimulating factor (M-CSF).

17. A peptide comprising an amino acid sequence comprising at least one lysin motif (LysM) domain represented by SEQ ID NO:10, and a Src homology 3 (SH3) domain represented by SEQ ID NO:26, wherein one of the at least one LysM domains represented by SEQ ID NO:10 is 15 amino acids upstream from the SH3 domain represented by SEQ ID NO:26, wherein the peptide is capable of inducing an immune response.

18. A peptide comprising an amino acid sequence comprising at least one lysin motif (LysM) domain represented by SEQ ID NO:11, and a Src homology 3 (SH3) domain represented by SEQ ID NO:26, wherein one of the at least one LysM domains represented by SEQ ID NO:11 is 15 amino acids upstream from the SH3 domain represented by SEQ ID NO:26, wherein the peptide is capable of inducing an immune response.

19. A peptide comprising an amino acid sequence comprising at least one LysM domain represented by SEQ ID NO:28, and an SH3 domain by SEQ ID NO:27, wherein one of the at least one LysM domains represented by SEQ ID NO:28 is 15 amino acids upstream from the SH3 domain represented by SEQ ID NO:27, wherein the peptide is capable of inducing an immune response.

20. A peptide comprising an amino acid sequence comprising at least one LysM domain represented by SEQ ID NO:12, and an SH3 domain by SEQ ID NO:27, wherein one of the at least one LysM domains represented by SEQ ID NO:12 is 15 amino acids upstream from the SH3 domain represented by SEQ ID NO:27, wherein the peptide is capable of inducing an immune response.

* * * * *

SEQUENCE LISTING

```
<160> NUMBER OF SEQ ID NOS: 28

<210> SEQ ID NO 1
<211> LENGTH: 450
<212> TYPE: PRT
<213> ORGANISM: Listeria monocytogenes

<400> SEQUENCE: 1

Thr Val Val Val Glu Ala Gly Asp Thr Leu Trp Gly Ile Ala Gln Ser
1               5                   10                  15

Lys Gly Thr Thr Val Asp Ala Ile Lys Lys Ala Asn Asn Leu Thr Thr
            20                  25                  30

Asp Lys Ile Val Pro Gly Gln Lys Leu Gln Val Asn Asn Glu Val Ala
        35                  40                  45

Ala Ala Glu Lys Thr Glu Lys Ser Val Ser Ala Thr Trp Leu Asn Val
    50                  55                  60

Arg Thr Gly Ala Gly Val Asp Asn Ser Ile Ile Thr Ser Ile Lys Gly
65                  70                  75                  80

Gly Thr Lys Val Thr Val Glu Thr Thr Glu Ser Asn Gly Trp His Lys
```

85                  90                  95
Ile Thr Tyr Asn Asp Gly Lys Thr Gly Phe Val Asn Gly Lys Tyr Leu
                100                 105                 110

Thr Asp Lys Ala Val Ser Thr Pro Val Ala Pro Thr Gln Glu Val Lys
                115                 120                 125

Lys Glu Thr Thr Thr Gln Gln Ala Ala Pro Val Ala Glu Thr Lys Thr
            130                 135                 140

Glu Val Lys Gln Thr Thr Gln Ala Thr Thr Pro Ala Pro Lys Val Ala
145                 150                 155                 160

Glu Thr Lys Glu Thr Pro Val Ile Asp Gln Asn Ala Thr Thr His Ala
                165                 170                 175

Val Lys Ser Gly Asp Thr Ile Trp Ala Leu Ser Val Lys Tyr Gly Val
                180                 185                 190

Ser Val Gln Asp Ile Met Ser Trp Asn Asn Leu Ser Ser Ser Ser Ile
                195                 200                 205

Tyr Val Gly Gln Lys Leu Ala Ile Lys Gln Thr Ala Asn Thr Ala Thr
                210                 215                 220

Pro Lys Ala Glu Val Lys Thr Glu Ala Pro Ala Ala Glu Lys Gln Ala
225                 230                 235                 240

Ala Pro Val Val Lys Glu Asn Thr Asn Thr Asn Thr Ala Thr Thr Glu
                245                 250                 255

Lys Lys Glu Thr Ala Thr Gln Gln Gln Thr Ala Pro Lys Ala Pro Thr
                260                 265                 270

Glu Ala Ala Lys Pro Ala Pro Ala Pro Ser Thr Asn Thr Asn Ala Asn
                275                 280                 285

Lys Thr Asn Thr Asn Thr Asn Thr Asn Thr Asn Thr Pro Ser Lys
                290                 295                 300

Asn Thr Asn Thr Asn Ser Asn Thr Asn Thr Asn Thr Asn Ser Asn Thr
305                 310                 315                 320

Asn Ala Asn Gln Gly Ser Ser Asn Asn Asn Ser Asn Ser Ser Ala Ser
                325                 330                 335

Ala Ile Ile Ala Glu Ala Gln Lys His Leu Gly Lys Ala Tyr Ser Trp
                340                 345                 350

Gly Gly Asn Gly Pro Thr Thr Phe Asp Ala Ser Gly Tyr Thr Lys Tyr
                355                 360                 365

Val Phe Ala Lys Ala Gly Ile Ser Leu Pro Arg Thr Ser Gly Ala Gln
                370                 375                 380

Tyr Ala Ser Thr Thr Arg Ile Ser Glu Ser Gln Ala Lys Pro Gly Asp
385                 390                 395                 400

Leu Val Phe Phe Asp Tyr Gly Ser Gly Ile Ser His Ile Gly Ile Tyr
                405                 410                 415

Val Gly Asn Gly Gln Met Ile Asn Ala Gln Asp Asn Gly Val Lys Tyr
                420                 425                 430

Asp Asn Ile His Gly Ser Gly Trp Gly Lys Tyr Leu Val Gly Phe Gly
                435                 440                 445

Arg Val
    450

<210> SEQ ID NO 2
<211> LENGTH: 450
<212> TYPE: PRT
<213> ORGANISM: Listeria monocytogenes

<400> SEQUENCE: 2

-continued

```
Thr Val Val Val Glu Ala Gly Asp Thr Leu Trp Gly Ile Ala Gln Ser
1               5                   10                  15

Lys Gly Thr Thr Val Asp Ala Ile Lys Lys Ala Asn Asn Leu Thr Thr
            20                  25                  30

Asp Lys Ile Val Pro Gly Gln Lys Leu Gln Val Asn Asn Glu Val Ala
            35                  40                  45

Ala Ala Glu Lys Thr Glu Lys Ser Val Ser Ala Thr Trp Leu Asn Val
50                  55                  60

Arg Thr Gly Ala Gly Val Asp Asn Ser Ile Ile Thr Ser Ile Lys Gly
65                  70                  75                  80

Gly Thr Lys Val Thr Val Glu Thr Thr Glu Ser Asn Gly Trp His Lys
                85                  90                  95

Ile Thr Tyr Asn Asp Gly Lys Thr Gly Phe Val Asn Gly Lys Tyr Leu
            100                 105                 110

Thr Asp Lys Ala Val Ser Thr Pro Val Ala Pro Thr Gln Glu Val Lys
            115                 120                 125

Lys Glu Thr Thr Thr Gln Gln Ala Ala Pro Val Ala Glu Thr Lys Thr
            130                 135                 140

Glu Val Lys Gln Thr Thr Gln Ala Thr Pro Ala Pro Lys Val Ala
145                 150                 155                 160

Glu Thr Lys Glu Thr Pro Val Ile Asp Gln Asn Ala Thr Thr His Ala
                165                 170                 175

Val Lys Ser Gly Asp Thr Ile Trp Ala Leu Ser Val Lys Tyr Gly Val
            180                 185                 190

Ser Val Gln Asp Ile Met Ser Trp Asn Asn Leu Ser Ser Ser Ser Ile
            195                 200                 205

Tyr Val Gly Gln Lys Leu Ala Ile Lys Gln Thr Ala Asn Thr Ala Thr
            210                 215                 220

Pro Lys Ala Glu Val Lys Thr Glu Ala Pro Ala Ala Glu Lys Gln Ala
225                 230                 235                 240

Ala Pro Val Val Lys Glu Asn Thr Asn Thr Asn Ala Thr Thr Glu
                245                 250                 255

Lys Lys Glu Thr Ala Thr Gln Gln Thr Ala Pro Lys Ala Pro Thr
            260                 265                 270

Glu Ala Ala Lys Pro Ala Pro Ala Pro Ser Thr Asn Thr Asn Ala Asn
            275                 280                 285

Lys Thr Asn Thr Asn Thr Asn Asn Thr Asn Thr Pro Ser Lys
            290                 295                 300

Asn Thr Asn Thr Asn Ser Asn Thr Asn Thr Asn Ser Asn Thr
305                 310                 315                 320

Asn Ala Asn Gln Gly Ser Ser Asn Asn Ser Asn Ser Ser Ala Ser
            325                 330                 335

Ala Ile Ile Ala Glu Ala Gln Lys His Leu Gly Lys Ala Tyr Ser Trp
            340                 345                 350

Gly Gly Asn Gly Pro Thr Thr Phe Asp Cys Ser Gly Tyr Thr Lys Tyr
            355                 360                 365

Val Phe Ala Lys Ala Gly Ile Ser Leu Pro Arg Thr Ser Gly Ala Gln
            370                 375                 380

Tyr Ala Ser Thr Thr Arg Ile Ser Glu Ser Gln Ala Lys Pro Gly Asp
385                 390                 395                 400

Leu Val Phe Phe Asp Tyr Gly Ser Gly Ile Ser His Ile Gly Ile Tyr
            405                 410                 415

Val Gly Asn Gly Gln Met Ile Asn Ala Gln Asp Asn Gly Val Lys Tyr
```

420              425              430
Asp Asn Ile His Gly Ser Gly Trp Gly Lys Tyr Leu Val Gly Phe Gly
        435              440              445
Arg Val
  450

<210> SEQ ID NO 3
<211> LENGTH: 1353
<212> TYPE: DNA
<213> ORGANISM: Listeria monocytogenes

<400> SEQUENCE: 3

| | | | | | |
|---|---|---|---|---|---|
| actgtagtag | tcgaagctgg | tgatactctt | tggggtatcg | cacaaagtaa | agggactact | 60 |
| gttgacgcaa | ttaaaaaagc | aaacaattta | acaacagata | aaatcgtacc | aggtcaaaaa | 120 |
| ttacaagtaa | ataatgaggt | tgctgctgct | gaaaaaacag | agaaatctgt | tagcgcaact | 180 |
| tggttaaacg | tccgtactgg | cgctggtgtt | gataacagta | ttattacgtc | catcaaaggt | 240 |
| ggaacaaaag | taactgttga | aacaaccgaa | tctaacggct | ggcacaaaat | tacttacaac | 300 |
| gatggaaaaa | ctggtttcgt | taacggtaaa | tacttaactg | acaaagcagt | aagcactcca | 360 |
| gttgcaccaa | cacaagaagt | gaaaaaagaa | actactactc | aacaagctgc | acctgttgca | 420 |
| gaaacaaaaa | ctgaagtaaa | acaaactaca | caagcaacta | cacctgcgcc | taaagtagca | 480 |
| gaaacgaaag | aaactccagt | aatagatcaa | atgctacta | cacgctgt | caaaagcggt | 540 |
| gacactattt | gggctttatc | cgtaaaatac | ggtgtttctg | ttcaagacat | tatgtcatgg | 600 |
| aataatttat | cttcttcttc | tatttatgta | ggtcaaaagc | ttgctattaa | acaaactgct | 660 |
| aacacagcta | ctccaaaagc | agaagtgaaa | acggaagctc | cagcagctga | aaaacaagca | 720 |
| gctccagtag | ttaaagaaaa | tactaacaca | atactgcta | ctacagagaa | aaaagaaaca | 780 |
| gcaacgcaac | aacaaacagc | acctaaagca | ccaacagaag | ctgcaaaacc | agctcctgca | 840 |
| ccatctacaa | acacaaatgc | taataaaacg | aatacaaata | caaatacaaa | caatactaat | 900 |
| acaccatcta | aaaatactaa | tacaaactca | aatactaata | cgaatacaaa | ctcaaatacg | 960 |
| aatgctaatc | aaggttcttc | caacaataac | agcaattcaa | gtgcaagtgc | tattattgct | 1020 |
| gaagctcaaa | acaccttgg | aaaagcttat | tcatggggtg | gtaacggacc | aactacattt | 1080 |
| gatgcctctg | ttacactaa | atatgtattt | gctaaagcgg | gtatctccct | tccacgtaca | 1140 |
| tctggcgcac | aatatgctag | cactacaaga | atttctgaat | ctcaagcaaa | acctggtgat | 1200 |
| ttagtattct | tcgactatgg | tagcggaatt | tctcacgttg | gtatttatgt | tggtaatggt | 1260 |
| caaatgatta | acgcgcaaga | caatggcgtt | aaatacgata | acatccacgg | ctctggctgg | 1320 |
| ggtaaatatc | tagttggctt | cggtcgcgta | taa | | | 1353 |

<210> SEQ ID NO 4
<211> LENGTH: 1353
<212> TYPE: DNA
<213> ORGANISM: Listeria monocytogenes

<400> SEQUENCE: 4

| | | | | | |
|---|---|---|---|---|---|
| actgtagtag | tcgaagctgg | tgatactctt | tggggtatcg | cacaaagtaa | agggactact | 60 |
| gttgacgcaa | ttaaaaaagc | aaacaattta | acaacagata | aaatcgtacc | aggtcaaaaa | 120 |
| ttacaagtaa | ataatgaggt | tgctgctgct | gaaaaaacag | agaaatctgt | tagcgcaact | 180 |
| tggttaaacg | tccgtactgg | cgctggtgtt | gataacagta | ttattacgtc | catcaaaggt | 240 |
| ggaacaaaag | taactgttga | aacaaccgaa | tctaacggct | ggcacaaaat | tacttacaac | 300 |

```
gatggaaaaa ctggtttcgt taacggtaaa tacttaactg acaaagcagt aagcactcca    360
gttgcaccaa cacaagaagt gaaaaaagaa actactactc aacaagctgc acctgttgca    420
gaaacaaaaa ctgaagtaaa acaaactaca caagcaacta cacctgcgcc taaagtagca    480
gaaacgaaag aaactccagt aatagatcaa atgctacta cacacgctgt caaaagcggt    540
gacactattt gggctttatc cgtaaaatac ggtgtttctg ttcaagacat tatgtcatgg    600
aataatttat cttcttcttc tatttatgta ggtcaaaagc ttgctattaa acaaactgct    660
aacacagcta ctccaaaagc agaagtgaaa acggaagctc agcagctga aaacaagca     720 gctccagtag ttaagaaaaa tactaacaca atactgcta ctacagagaa aaagaaaca    780 gcaacgcaac aacaaacagc acctaaagca ccaacagaag ctgcaaaacc agctcctgca    840
ccatctacaa acacaaatgc taataaaacg aatacaaata caaatacaaa caatactaat    900
acaccatcta aaatactaa tacaaactca aatactaata cgaatacaaa ctcaaatacg    960
aatgctaatc aaggttcttc caacaataac agcaattcaa gtgcaagtgc tattattgct   1020
gaagctcaaa acaccttgg aaaagcttat tcatggggtg gtaacggacc aactacattt   1080
gattgctctg gttacactaa atatgtattt gctaaagcgg gtatctccct tccacgtaca   1140
tctggcgcac aatatgctag cactacaaga atttctgaat ctcaagcaaa acctggtgat   1200
ttagtattct tcgactatgg tagcggaatt tctcacgttg gtatttatgt tggtaatggt   1260
caaatgatta acgcgcaaga caatggcgtt aaatacgata catccacgg ctctggctgg    1320 ggtaaatatc tagttggctt cggtcgcgta taa                                1353

<210> SEQ ID NO 5
<211> LENGTH: 476
<212> TYPE: PRT
<213> ORGANISM: Listeria monocytogenes

<400> SEQUENCE: 5

Met Lys Lys Ala Thr Ile Ala Ala Thr Ala Gly Ile Ala Val Thr Ala
1               5                   10                  15

Phe Ala Ala Pro Thr Ile Ala Ser Ala Ser Thr Val Val Glu Ala
            20                  25                  30

Gly Asp Thr Leu Trp Gly Ile Ala Gln Ser Lys Gly Thr Thr Val Asp
        35                  40                  45

Ala Ile Lys Lys Ala Asn Asn Leu Thr Thr Asp Lys Ile Val Pro Gly
    50                  55                  60

Gln Lys Leu Gln Val Asn Asn Glu Val Ala Ala Glu Lys Thr Glu
65                  70                  75                  80

Lys Ser Val Ser Ala Thr Trp Leu Asn Val Arg Thr Gly Ala Gly Val
                85                  90                  95

Asp Asn Ser Ile Ile Thr Ser Ile Lys Gly Gly Thr Lys Val Thr Val
            100                 105                 110

Glu Thr Thr Glu Ser Asn Gly Trp His Lys Ile Thr Tyr Asn Asp Gly
        115                 120                 125

Lys Thr Gly Phe Val Asn Gly Lys Tyr Leu Thr Asp Lys Ala Val Ser
    130                 135                 140

Thr Pro Val Ala Pro Thr Gln Glu Val Lys Lys Glu Thr Thr Gln
145                 150                 155                 160

Gln Ala Ala Pro Val Ala Glu Thr Lys Thr Glu Val Lys Gln Thr Thr
                165                 170                 175

Gln Ala Thr Thr Pro Ala Pro Lys Val Ala Glu Thr Lys Glu Thr Pro
```

```
              180                 185                 190
Val Ile Asp Gln Asn Ala Thr Thr His Ala Val Lys Ser Gly Asp Thr
            195                 200                 205

Ile Trp Ala Leu Ser Val Lys Tyr Gly Val Ser Val Gln Asp Ile Met
            210                 215                 220

Ser Trp Asn Asn Leu Ser Ser Ser Ile Tyr Val Gly Gln Lys Leu
225                 230                 235                 240

Ala Ile Lys Gln Thr Ala Asn Thr Ala Thr Pro Lys Ala Glu Val Lys
                245                 250                 255

Thr Glu Ala Pro Ala Ala Glu Lys Gln Ala Ala Pro Val Val Lys Glu
            260                 265                 270

Asn Thr Asn Thr Asn Thr Ala Thr Glu Lys Lys Glu Thr Ala Thr
            275                 280                 285

Gln Gln Gln Thr Ala Pro Lys Ala Pro Thr Glu Ala Ala Lys Pro Ala
            290                 295                 300

Pro Ala Pro Ser Thr Asn Thr Asn Ala Asn Lys Thr Asn Thr Asn Thr
305                 310                 315                 320

Asn Thr Asn Asn Thr Asn Thr Pro Ser Lys Asn Thr Asn Thr Asn Ser
                325                 330                 335

Asn Thr Asn Thr Asn Thr Asn Ser Asn Thr Asn Ala Asn Gln Gly Ser
                340                 345                 350

Ser Asn Asn Asn Ser Asn Ser Ser Ala Ser Ala Ile Ile Ala Glu Ala
            355                 360                 365

Gln Lys His Leu Gly Lys Ala Tyr Ser Trp Gly Gly Asn Gly Pro Thr
            370                 375                 380

Thr Phe Asp Cys Ser Gly Tyr Thr Lys Tyr Val Phe Ala Lys Ala Gly
385                 390                 395                 400

Ile Ser Leu Pro Arg Thr Ser Gly Ala Gln Tyr Ala Ser Thr Thr Arg
                405                 410                 415

Ile Ser Glu Ser Gln Ala Lys Pro Gly Asp Leu Val Phe Phe Asp Tyr
            420                 425                 430

Gly Ser Gly Ile Ser His Val Gly Ile Tyr Val Gly Asn Gly Gln Met
            435                 440                 445

Ile Asn Ala Gln Asp Asn Gly Val Lys Tyr Asp Asn Ile His Gly Ser
            450                 455                 460

Gly Trp Gly Lys Tyr Leu Val Gly Phe Gly Arg Val
465                 470                 475

<210> SEQ ID NO 6
<211> LENGTH: 476
<212> TYPE: PRT
<213> ORGANISM: Listeria monocytogenes

<400> SEQUENCE: 6

Met Lys Lys Ala Thr Ile Ala Ala Thr Ala Gly Ile Ala Val Thr Ala
1               5                   10                  15

Phe Ala Ala Pro Thr Ile Ala Ser Ala Ser Thr Val Val Glu Ala
                20                  25                  30

Gly Asp Thr Leu Trp Gly Ile Ala Gln Ser Lys Gly Thr Thr Val Asp
            35                  40                  45

Ala Ile Lys Lys Ala Asn Asn Leu Thr Thr Asp Lys Ile Val Pro Gly
        50                  55                  60

Gln Lys Leu Gln Val Asn Asn Glu Val Ala Ala Ala Glu Lys Thr Glu
65                  70                  75                  80
```

-continued

```
Lys Ser Val Ser Ala Thr Trp Leu Asn Val Arg Thr Gly Ala Gly Val
                 85                  90                  95

Asp Asn Ser Ile Ile Thr Ser Ile Lys Gly Gly Thr Lys Val Thr Val
            100                 105                 110

Glu Thr Thr Glu Ser Asn Gly Trp His Lys Ile Thr Tyr Asn Asp Gly
        115                 120                 125

Lys Thr Gly Phe Val Asn Gly Lys Tyr Leu Thr Asp Lys Ala Val Ser
    130                 135                 140

Thr Pro Val Ala Pro Thr Gln Glu Val Lys Lys Glu Thr Thr Thr Gln
145                 150                 155                 160

Gln Ala Ala Pro Val Ala Glu Thr Lys Thr Glu Val Lys Gln Thr Thr
                165                 170                 175

Gln Ala Thr Thr Pro Ala Pro Lys Val Ala Glu Thr Lys Glu Thr Pro
            180                 185                 190

Val Ile Asp Gln Asn Ala Thr Thr His Ala Val Lys Ser Gly Asp Thr
        195                 200                 205

Ile Trp Ala Leu Ser Val Lys Tyr Gly Val Ser Val Gln Asp Ile Met
    210                 215                 220

Ser Trp Asn Asn Leu Ser Ser Ser Ile Tyr Val Gly Gln Lys Leu
225                 230                 235                 240

Ala Ile Lys Gln Thr Ala Asn Thr Ala Thr Pro Lys Ala Glu Val Lys
                245                 250                 255

Thr Glu Ala Pro Ala Ala Glu Lys Gln Ala Ala Pro Val Val Lys Glu
            260                 265                 270

Asn Thr Asn Thr Asn Thr Ala Thr Thr Glu Lys Lys Glu Thr Ala Thr
        275                 280                 285

Gln Gln Gln Thr Ala Pro Lys Ala Pro Thr Glu Ala Ala Lys Pro Ala
    290                 295                 300

Pro Ala Pro Ser Thr Asn Thr Asn Ala Asn Lys Thr Asn Thr Asn Thr
305                 310                 315                 320

Asn Thr Asn Asn Thr Asn Thr Pro Ser Lys Asn Thr Asn Thr Asn Ser
                325                 330                 335

Asn Thr Asn Thr Asn Thr Asn Ser Asn Thr Asn Ala Asn Gln Gly Ser
            340                 345                 350

Ser Asn Asn Asn Ser Asn Ser Ser Ala Ser Ala Ile Ile Ala Glu Ala
        355                 360                 365

Gln Lys His Leu Gly Lys Ala Tyr Ser Trp Gly Gly Asn Gly Pro Thr
    370                 375                 380

Thr Phe Asp Ala Ser Gly Tyr Thr Lys Tyr Val Phe Ala Lys Ala Gly
385                 390                 395                 400

Ile Ser Leu Pro Arg Thr Ser Gly Ala Gln Tyr Ala Ser Thr Thr Arg
                405                 410                 415

Ile Ser Glu Ser Gln Ala Lys Pro Gly Asp Leu Val Phe Phe Asp Tyr
            420                 425                 430

Gly Ser Gly Ile Ser His Val Gly Ile Tyr Val Gly Asn Gly Gln Met
        435                 440                 445

Ile Asn Ala Gln Asp Asn Gly Val Lys Tyr Asp Asn Ile His Gly Ser
    450                 455                 460

Gly Trp Gly Lys Tyr Leu Val Gly Phe Gly Arg Val
465                 470                 475
```

<210> SEQ ID NO 7
<211> LENGTH: 476
<212> TYPE: PRT

<213> ORGANISM: Artificial Sequence
<220> FEATURE:
<223> OTHER INFORMATION: Listeria monocytogenes p60 derivative

<400> SEQUENCE: 7

```
Met Lys Lys Ala Thr Ile Ala Ala Thr Ala Gly Ile Ala Val Thr Ala
1               5                   10                  15

Phe Ala Ala Pro Thr Ile Ala Ser Ala Ser Thr Val Val Glu Ala
                20                  25                  30

Gly Asp Thr Leu Trp Gly Ile Ala Gln Ser Lys Gly Thr Thr Val Asp
                35                  40                  45

Ala Ile Lys Lys Ala Asn Asn Leu Thr Thr Asp Lys Ile Val Pro Gly
50                  55                  60

Gln Lys Leu Gln Val Asn Asn Glu Val Ala Ala Ala Glu Lys Thr Glu
65                  70                  75                  80

Lys Ser Val Ser Ala Thr Trp Leu Asn Val Arg Thr Gly Ala Gly Val
                85                  90                  95

Asp Asn Ser Ile Ile Thr Ser Ile Lys Gly Gly Thr Lys Val Thr Val
                100                 105                 110

Glu Thr Thr Glu Ser Asn Gly Trp His Lys Ile Thr Tyr Asn Asp Gly
                115                 120                 125

Lys Thr Gly Phe Val Asn Gly Lys Tyr Leu Thr Asp Lys Ala Val Ser
130                 135                 140

Thr Pro Val Ala Pro Thr Gln Glu Val Lys Lys Glu Thr Thr Thr Gln
145                 150                 155                 160

Gln Ala Ala Pro Val Ala Glu Thr Lys Thr Glu Val Lys Gln Thr Thr
                165                 170                 175

Gln Ala Thr Thr Pro Ala Pro Lys Val Ala Glu Thr Lys Glu Thr Pro
                180                 185                 190

Val Ile Asp Gln Asn Ala Thr Thr His Ala Val Lys Ser Gly Asp Thr
                195                 200                 205

Ile Trp Ala Leu Ser Val Lys Tyr Gly Val Ser Val Gln Asp Ile Met
210                 215                 220

Ser Trp Asn Asn Leu Ser Ser Ser Ser Ile Tyr Val Gly Gln Lys Leu
225                 230                 235                 240

Ala Ile Lys Gln Thr Ala Asn Thr Ala Thr Pro Lys Ala Glu Val Lys
                245                 250                 255

Thr Glu Ala Pro Ala Ala Glu Lys Gln Ala Ala Pro Val Val Lys Glu
                260                 265                 270

Asn Thr Asn Thr Asn Thr Ala Thr Thr Glu Lys Lys Glu Thr Ala Thr
                275                 280                 285

Gln Gln Gln Thr Ala Pro Lys Ala Pro Thr Glu Ala Ala Lys Pro Ala
                290                 295                 300

Pro Ala Pro Ser Thr Asn Thr Asn Ala Asn Lys Thr Asn Thr Asn Thr
305                 310                 315                 320

Asn Thr Asn Asn Thr Asn Thr Pro Ser Lys Asn Thr Asn Thr Asn Ser
                325                 330                 335

Asn Thr Asn Thr Asn Thr Asn Ser Asn Thr Asn Ala Asn Gln Gly Ser
                340                 345                 350

Ser Asn Asn Asn Ser Asn Ser Ser Ala Ser Ala Ile Ile Ala Glu Ala
                355                 360                 365

Gln Lys His Leu Gly Lys Ala Tyr Ser Trp Gly Gly Asn Gly Pro Thr
                370                 375                 380

Thr Phe Asp Ala Ser Gly Tyr Thr Lys Tyr Val Phe Ala Lys Ala Gly
```

```
                385                 390                 395                 400
Ile Ser Leu Pro Arg Thr Ser Gly Ala Gln Tyr Ala Ser Thr Thr Arg
                405                 410                 415
Ile Ser Glu Ser Gln Ala Lys Pro Gly Asp Leu Val Phe Phe Asp Tyr
                420                 425                 430
Gly Ser Gly Ile Ser Ala Val Gly Ile Tyr Val Gly Asn Gly Gln Met
                435                 440                 445
Ile Asn Ala Gln Asp Asn Gly Val Lys Tyr Asp Asn Ile Ala Gly Ser
                450                 455                 460
Gly Trp Gly Lys Tyr Leu Val Gly Phe Gly Arg Val
465                 470                 475

<210> SEQ ID NO 8
<211> LENGTH: 114
<212> TYPE: PRT
<213> ORGANISM: Listeria monocytogenes

<400> SEQUENCE: 8

Ser Thr Val Val Val Glu Ala Gly Asp Thr Leu Trp Gly Ile Ala Gln
1               5                   10                  15
Ser Lys Gly Thr Thr Val Asp Ala Ile Lys Lys Ala Asn Asn Leu Thr
                20                  25                  30
Thr Asp Lys Ile Val Pro Gly Gln Lys Leu Gln Val Asn Asn Glu Val
                35                  40                  45
Ala Ala Ala Glu Lys Thr Glu Lys Ser Val Ser Ala Thr Trp Leu Asn
                50                  55                  60
Val Arg Thr Gly Ala Gly Val Asp Asn Ser Ile Ile Thr Ser Ile Lys
65                  70                  75                  80
Gly Gly Thr Lys Val Thr Val Glu Thr Thr Glu Ser Asn Gly Trp His
                85                  90                  95
Lys Ile Thr Tyr Asn Asp Gly Lys Thr Gly Phe Val Asn Gly Lys Tyr
                100                 105                 110
Leu Thr

<210> SEQ ID NO 9
<211> LENGTH: 159
<212> TYPE: PRT
<213> ORGANISM: Listeria monocytogenes

<400> SEQUENCE: 9

Thr Trp Leu Asn Val Arg Thr Gly Ala Gly Val Asp Asn Ser Ile Ile
1               5                   10                  15
Thr Ser Ile Lys Gly Gly Thr Lys Val Thr Val Glu Thr Thr Glu Ser
                20                  25                  30
Asn Gly Trp His Lys Ile Thr Tyr Asn Asp Gly Lys Thr Gly Phe Val
                35                  40                  45
Asn Gly Lys Tyr Leu Thr Asp Lys Ala Val Ser Thr Pro Val Ala Pro
                50                  55                  60
Thr Gln Glu Val Lys Lys Glu Thr Thr Thr Gln Gln Ala Ala Pro Val
65                  70                  75                  80
Ala Glu Thr Lys Thr Glu Val Lys Gln Thr Thr Gln Ala Thr Thr Pro
                85                  90                  95
Ala Pro Lys Val Ala Glu Thr Lys Glu Thr Pro Val Ile Asp Gln Asn
                100                 105                 110
Ala Thr Thr His Ala Val Lys Ser Gly Asp Thr Ile Trp Ala Leu Ser
                115                 120                 125
```

```
Val Lys Tyr Gly Val Ser Val Gln Asp Ile Met Ser Trp Asn Asn Leu
    130                 135                 140

Ser Ser Ser Ser Ile Tyr Val Gly Gln Lys Leu Ala Ile Lys Gln
145                 150                 155

<210> SEQ ID NO 10
<211> LENGTH: 44
<212> TYPE: PRT
<213> ORGANISM: Listeria monocytogenes

<400> SEQUENCE: 10

Ser Thr Val Val Glu Ala Gly Asp Thr Leu Trp Gly Ile Ala Gln
1               5                   10                  15

Ser Lys Gly Thr Thr Val Asp Ala Ile Lys Lys Ala Asn Asn Leu Thr
                20                  25                  30

Thr Asp Lys Ile Val Pro Gly Gln Lys Leu Gln Val
            35                  40

<210> SEQ ID NO 11
<211> LENGTH: 44
<212> TYPE: PRT
<213> ORGANISM: Listeria monocytogenes

<400> SEQUENCE: 11

His Ala Val Lys Ser Gly Asp Thr Ile Trp Ala Leu Ser Val Lys Tyr
1               5                   10                  15

Gly Val Ser Val Gln Asp Ile Met Ser Trp Asn Asn Leu Ser Ser Ser
                20                  25                  30

Ser Ile Tyr Val Gly Gln Lys Leu Ala Ile Lys Gln
            35                  40

<210> SEQ ID NO 12
<211> LENGTH: 42
<212> TYPE: PRT
<213> ORGANISM: Artificial Sequence
<220> FEATURE:
<223> OTHER INFORMATION: Listeria monocytogenes p60 peptide consensus
      regions
<220> FEATURE:
<221> NAME/KEY: MISC_FEATURE
<222> LOCATION: (1)..(6)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (12)..(14)
<223> OTHER INFORMATION: Xaa can be any naturally occurring amino acid
<220> FEATURE:
<221> NAME/KEY: MISC_FEATURE
<222> LOCATION: (16)..(25)
<223> OTHER INFORMATION: Xaa can be any naturally occurring amino acid
<220> FEATURE:
<221> NAME/KEY: MISC_FEATURE
<222> LOCATION: (29)..(34)
<223> OTHER INFORMATION: Xaa can be any naturally occurring amino acid
<220> FEATURE:
<221> NAME/KEY: MISC_FEATURE
<222> LOCATION: (36)..(36)
<223> OTHER INFORMATION: Xaa can be any naturally occurring amino acid
<220> FEATURE:
<221> NAME/KEY: MISC_FEATURE
<222> LOCATION: (41)..(42)
<223> OTHER INFORMATION: Xaa can be any naturally occurring amino acid

<400> SEQUENCE: 12
```

```
Xaa Xaa Xaa Xaa Xaa Xaa Gly Asp Thr Xaa Trp Xaa Xaa Lys Xaa
1               5                   10                  15

Xaa Xaa Xaa Xaa Xaa Xaa Xaa Xaa Asn Asn Leu Xaa Xaa Xaa Xaa
            20                  25                  30

Xaa Xaa Val Xaa Gly Gln Lys Leu Xaa Xaa
        35                  40

```
Lys Lys Glu Thr Thr Thr Gln Gln Ala Ala Pro Val Ala Glu Thr Lys
        130                 135                 140
Thr Glu Val Lys Gln Thr Thr Gln Ala Thr Thr Pro Ala Pro Lys Val
145                 150                 155                 160
Ala Glu Thr Lys Glu Thr Pro Val Ile Asp Gln Asn Ala Thr Thr His
                165                 170                 175
Ala Val Lys Ser Gly Asp Thr Ile Trp Ala Leu Ser Val Lys Tyr Gly
            180                 185                 190
Val Ser Val Gln Asp Ile Met Ser Trp Asn Asn Leu Ser Ser Ser Ser
        195                 200                 205
Ile Tyr Val Gly Gln Lys Leu Ala Ile Lys Gln Thr Ala Asn Thr Ala
    210                 215                 220
Thr Pro Lys Ala Glu Val Lys Thr Glu Ala Pro Ala Ala Glu Lys Gln
225                 230                 235                 240
Ala Ala Pro Val Val Lys Glu Asn Thr Asn Thr Asn Thr Ala Thr Thr
                245                 250                 255
Glu Lys Lys Glu Thr Ala Thr Gln Gln Gln Thr Ala Pro Lys Ala Pro
            260                 265                 270
Thr Glu Ala Ala Lys Pro Ala Pro Ala Pro Ser Thr Asn
        275                 280                 285

<210> SEQ ID NO 15
<211> LENGTH: 501
<212> TYPE: DNA
<213> ORGANISM: Listeria monocytogenes

<400> SEQUENCE: 15
acaaatgcta ataaaacgaa tacaaataca aatacaaaca atactaatac accatctaaa      60
aatactaata caaactcaaa tactaatacg aatacaaact caaatacgaa tgctaatcaa     120
ggttcttcca acaataacag caattcaagt gcaagtgcta ttattgctga agctcaaaaa     180
caccttggaa aagcttattc atggggtggt aacggaccaa ctacatttga ttgctctggt     240
tacactaaat atgtatttgc taaagcgggt atctcccttc cacgtacatc tggcgcacaa     300
tatgctagca ctacaagaat ttctgaatct caagcaaaac ctggtgattt agtattcttc     360
gactatggta gcggaattttc tcacgttggt atttatgttg gtaatggtca aatgattaac     420
gcgcaagaca atggcgttaa atacgataac atccacggct ctggctgggg taaatatcta     480
gttggcttcg gtcgcgtata a                                               501

<210> SEQ ID NO 16
<211> LENGTH: 166
<212> TYPE: PRT
<213> ORGANISM: Listeria monocytogenes

<400> SEQUENCE: 16

Thr Asn Ala Asn Lys Thr Asn Thr Asn Thr Asn Thr Asn Asn Thr Asn
1               5                   10                  15
Thr Pro Ser Lys Asn Thr Asn Thr Asn Ser Asn Thr Asn Thr Asn Thr
            20                  25                  30
Asn Ser Asn Thr Asn Ala Asn Gln Gly Ser Ser Asn Asn Asn Ser Asn
        35                  40                  45
Ser Ser Ala Ser Ala Ile Ile Ala Glu Ala Gln Lys His Leu Gly Lys
    50                  55                  60
Ala Tyr Ser Trp Gly Gly Asn Gly Pro Thr Thr Phe Asp Cys Ser Gly
65                  70                  75                  80
```

Tyr Thr Lys Tyr Val Phe Ala Lys Ala Gly Ile Ser Leu Pro Arg Thr
            85                  90                  95

Ser Gly Ala Gln Tyr Ala Ser Thr Thr Arg Ile Ser Glu Ser Gln Ala
        100                 105                 110

Lys Pro Gly Asp Leu Val Phe Phe Asp Tyr Gly Ser Gly Ile Ser His
        115                 120                 125

Val Gly Ile Tyr Val Gly Asn Gly Gln Met Ile Asn Ala Gln Asp Asn
        130                 135                 140

Gly Val Lys Tyr Asp Asn Ile His Gly Ser Gly Trp Gly Lys Tyr Leu
145                 150                 155                 160

Val Gly Phe Gly Arg Val
            165

<210> SEQ ID NO 17
<211> LENGTH: 34
<212> TYPE: DNA
<213> ORGANISM: Artificial Sequence
<220> FEATURE:
<223> OTHER INFORMATION: p60 primer

<400> SEQUENCE: 17
agggatccat gaaaaagcaa ctatcgcggc taca                                34

<210> SEQ ID NO 18
<211> LENGTH: 48
<212> TYPE: DNA
<213> ORGANISM: Artificial Sequence
<220> FEATURE:
<223> OTHER INFORMATION: p60 primer

<400> SEQUENCE: 18
atgatgatgg tgatggtgat ggtgatggct tgcggatgcg attgttgg                 48

<210> SEQ ID NO 19
<211> LENGTH: 42
<212> TYPE: DNA
<213> ORGANISM: Artificial Sequence
<220> FEATURE:
<223> OTHER INFORMATION: p60 primer

<400> SEQUENCE: 19
agccatcacc atcaccatca cgtagtcgaa gctggtactc tt                       42

<210> SEQ ID NO 20
<211> LENGTH: 40
<212> TYPE: DNA
<213> ORGANISM: Artificial Sequence
<220> FEATURE:
<223> OTHER INFORMATION: p60 primer

<400> SEQUENCE: 20
agctcgagta taccgcaccg aagccaacta gatatttacc                          40

<210> SEQ ID NO 21
<211> LENGTH: 30
<212> TYPE: DNA
<213> ORGANISM: Artificial Sequence
<220> FEATURE:
<223> OTHER INFORMATION: p60 primer

<400> SEQUENCE: 21
actgtagtag tcgaagctgg tgatactctt                                     30

```
<210> SEQ ID NO 22
<211> LENGTH: 30
<212> TYPE: DNA
<213> ORGANISM: Artificial Sequence
<220> FEATURE:
<223> OTHER INFORMATION: p60 primer

<400> SEQUENCE: 22
aagagtatca ccagcttcga ctactacagt                              30

<210> SEQ ID NO 23
<211> LENGTH: 37
<212> TYPE: DNA
<213> ORGANISM: Artificial Sequence
<220> FEATURE:
<223> OTHER INFORMATION: p60 primer

<400> SEQUENCE: 23
ccaactccat ttgatgcttc tggttacact aaatatg                      37

<210> SEQ ID NO 24
<211> LENGTH: 37
<212> TYPE: DNA
<213> ORGANISM: Artificial Sequence
<220> FEATURE:
<223> OTHER INFORMATION: p60 primer

<400> SEQUENCE: 24
catatttagt gtaaccagaa gcatcaaatg tagttgg                      37

<210> SEQ ID NO 25
<211> LENGTH: 46
<212> TYPE: PRT
<213> ORGANISM: Artificial Sequence
<220> FEATURE:
<223> OTHER INFORMATION: derived from Listeria monocytogenes
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (14)..(16)
<223> OTHER INFORMATION: Xaa can be any naturally occurring amino acid
<220> FEATURE:
<221> NAME/KEY: MISC_FEATURE
<222> LOCATION: (18)..(19)
<223> OTHER INFORMATION: Xaa can be any naturally occurring amino acid
<220> FEATURE:
<221> NAME/KEY: MISC_FEATURE
<222> LOCATION: (22)..(25)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Xaa can be any naturally occurring amino acid
<220> FEATURE:
<221> NAME/KEY: MISC_FEATURE
<222> LOCATION: (29)..(29)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Xaa can be any naturally occurring amino acid
```

```
<220> FEATURE:
<221> NAME/KEY: MISC_FEATURE
<222> LOCATION: (33)..(33)
<223> OTHER INFORMATION: Xaa can be any naturally occurring amino acid
<220> FEATURE:
<221> NAME/KEY: MISC_FEATURE
<222> LOCATION: (35)..(35)
<223> OTHER INFORMATION: Xaa can be any naturally occurring amino acid
<220> FEATURE:
<221> NAME/KEY: MISC_FEATURE
<222> LOCATION: (39)..(40)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 25

Tyr Xaa Val Xaa Ala Gly Asp Thr Leu Trp Xaa Ile Ala Xaa Xaa Xaa
1               5                   10                  15

Gly Xaa Xaa Val Asp Xaa Xaa Xaa Xaa Leu Xaa Lys Xaa Asn Xaa Leu
            20                  25                  30

Xaa Thr Xaa Lys Leu Val Xaa Xaa Gly Gln Xaa Leu Xaa Ile
        35                  40                  45

<210> SEQ ID NO 26
<211> LENGTH: 51
<212> TYPE: PRT
<213> ORGANISM: Artificial Sequence
<220> FEATURE:
<223> OTHER INFORMATION: derived from Listeria monocytogenes
<220> FEATURE:
<221> NAME/KEY: MISC_FEATURE
<222> LOCATION: (5)..(12)
<223> OTHER INFORMATION: Xaa can be any naturally occurring amino acid
<220> FEATURE:
<221> NAME/KEY: MISC_FEATURE
<222> LOCATION: (15)..(16)
<223> OTHER INFORMATION: Xaa can be any naturally occurring amino acid
<220> FEATURE:
<221> NAME/KEY: MISC_FEATURE
<222> LOCATION: (18)..(22)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Xaa can be any naturally occurring amino acid
<220> FEATURE:
<221> NAME/KEY: MISC_FEATURE
<222> LOCATION: (26)..(29)
<223> OTHER INFORMATION: Xaa can be any naturally occurring amino acid
<220> FEATURE:
<221> NAME/KEY: MISC_FEATURE
<222> LOCATION: (31)..(32)
<223> OTHER INFORMATION: Xaa can be any naturally occurring amino acid
<220> FEATURE:
<221> NAME/KEY: MISC_FEATURE
<222> LOCATION: (34)..(34)
<223> OTHER INFORMATION: Xaa can be any naturally occurring amino acid
<220> FEATURE:
<221> NAME/KEY: MISC_FEATURE
<222> LOCATION: (37)..(37)
<223> OTHER INFORMATION: Xaa can be any naturally occurring amino acid
<220> FEATURE:
<221> NAME/KEY: MISC_FEATURE
<222> LOCATION: (39)..(40)
<223> OTHER INFORMATION: Xaa can be any naturally occurring amino acid
<220> FEATURE:
<221> NAME/KEY: MISC_FEATURE
<222> LOCATION: (42)..(43)
<223> OTHER INFORMATION: Xaa can be any naturally occurring amino acid
```

```
<220> FEATURE:
<221> NAME/KEY: MISC_FEATURE
<222> LOCATION: (47)..(49)
<223> OTHER INFORMATION: Xaa can be any naturally occurring amino acid

<400> SEQUENCE: 26

Leu Asn Val Arg Xaa Xaa Xaa Xaa Xaa Xaa Xaa Ile Ile Xaa Xaa
1               5                   10                  15

Leu Xaa Xaa Xaa Xaa Xaa Val Xaa Val Xaa Xaa Xaa Xaa Gly Xaa Xaa
            20                  25                  30

Trp Xaa Lys Ile Xaa Phe Xaa Xaa Gly Xaa Xaa Gly Tyr Val Xaa Xaa
        35                  40                  45

Xaa Tyr Val
    50

<210> SEQ ID NO 27
<211> LENGTH: 54
<212> TYPE: PRT
<213> ORGANISM: Listeria monocytogenes

<400> SEQUENCE: 27

Thr Trp Leu Asn Val Arg Thr Gly Ala Gly Val Asp Asn Ser Ile Ile
1               5                   10                  15

Thr Ser Ile Lys Lys Gly Thr Lys Val Thr Val Glu Thr Thr Glu Ser
            20                  25                  30

Asn Gly Trp His Lys Ile Thr Tyr Asn Asp Gly Lys Thr Gly Phe Val
        35                  40                  45

Asn Gly Lys Tyr Leu Thr
    50

<210> SEQ ID NO 28
<211> LENGTH: 64
<212> TYPE: PRT
<213> ORGANISM: Artificial Sequence
<220> FEATURE:
<223> OTHER INFORMATION: Dervived from Listeria monocytogenes
<220> FEATURE:
<221> NAME/KEY: MISC_FEATURE
<222> LOCATION: (1)..(10)
<223> OTHER INFORMATION: Xaa is any naturally occuring amino acid,
      present 1 and upto 10 times
<220> FEATURE:
<221> NAME/KEY: MISC_FEATURE
<222> LOCATION: (14)..(18)
<223> OTHER INFORMATION: Xaa is any naturally occuring amino acid,
      present 1 and up to 5 times
<220> FEATURE:
<221> NAME/KEY: MISC_FEATURE
<222> LOCATION: (20)..(24)
<223> OTHER INFORMATION: Xaa is any naturally occuring amino acid,
      present 1 and up to 5 times
<220> FEATURE:
<221> NAME/KEY: MISC_FEATURE
<222> LOCATION: (26)..(40)
<223> OTHER INFORMATION: Xaa is any naturally occuring amino acid,
      present 5 and up to 15 times
<220> FEATURE:
<221> NAME/KEY: MISC_FEATURE
<222> LOCATION: (44)..(53)
<223> OTHER INFORMATION: Xaa is any naturally occuring amino acid,
      present 1 and up to 10 times
<220> FEATURE:
<221> NAME/KEY: MISC_FEATURE
<222> LOCATION: (55)..(55)
<223> OTHER INFORMATION: Xaa is any naturally occuring amino acid
<220> FEATURE:
<221> NAME/KEY: MISC_FEATURE
<222> LOCATION: (60)..(64)
<223> OTHER INFORMATION: Xaa is any naturally occuring amino acid,
```

-continued

```
   present 1 and up to 5 times

<400> SEQUENCE: 28

Xaa Xaa Xaa Xaa Xaa Xaa Xaa Xaa Xaa Xaa Gly Asp Thr Xaa Xaa Xaa
1               5                   10                  15

Xaa Xaa Trp Xaa Xaa Xaa Xaa Xaa Lys Xaa Xaa Xaa Xaa Xaa Xaa Xaa
            20                  25                  30

Xaa Xaa Xaa Xaa Xaa Xaa Xaa Xaa Asn Asn Leu Xaa Xaa Xaa Xaa Xaa
            35                  40                  45

Xaa Xaa Xaa Xaa Xaa Val Xaa Gly Gln Lys Leu Xaa Xaa Xaa Xaa Xaa
        50              55                  60
```